US010005845B2

(12) United States Patent
Loustau et al.

(10) Patent No.: US 10,005,845 B2
(45) Date of Patent: Jun. 26, 2018

(54) ANTIBODIES AND FRAGMENTS THEREOF RAISED AGAINST THE ALPHA-3 DOMAIN OF HLA-G PROTEIN, METHODS AND MEANS FOR THEIR PREPARATION, AND USES THEREOF

(71) Applicant: INVECTYS, Paris (FR)

(72) Inventors: Maria de las Nieves Loustau, Paris (FR); Julien Caumartin, Le Vesinet (FR); Pierre Langlade-Demoyen, Neuilly sur Seine (FR)

(73) Assignee: INVECTYS, Paris (FR)

( * ) Notice: Subject to any disclaimer, the term of this patent is extended or adjusted under 35 U.S.C. 154(b) by 0 days. days.

(21) Appl. No.: 14/442,320

(22) PCT Filed: Nov. 12, 2013

(86) PCT No.: PCT/EP2013/073648
§ 371 (c)(1),
(2) Date: May 12, 2015

(87) PCT Pub. No.: WO2014/072534
PCT Pub. Date: May 15, 2014

(65) Prior Publication Data
US 2016/0272724 A1 Sep. 22, 2016

(30) Foreign Application Priority Data
Nov. 12, 2012 (EP) .................................... 12306398

(51) Int. Cl.

| | |
|---|---|
| ***C07K 16/34*** | (2006.01) |
| ***C07K 14/74*** | (2006.01) |
| ***C07K 16/28*** | (2006.01) |
| ***A61K 39/00*** | (2006.01) |

(52) U.S. Cl.
CPC .......... *C07K 16/34* (2013.01); *A61K 39/0005* (2013.01); *C07K 14/70539* (2013.01); *C07K 16/2833* (2013.01); *A61K 2039/53* (2013.01); *A61K 2039/585* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 2007/0259403 A1 | 11/2007 | Miyagawa et al. | | |
| 2010/0285019 A1* | 11/2010 | Masternak | ........... | C07K 16/244 424/142.1 |
| 2011/0135672 A1* | 6/2011 | Horuzsko | ............ | C07K 16/248 424/185.1 |

FOREIGN PATENT DOCUMENTS

| | | | | |
|---|---|---|---|---|
| WO | 99/42128 A1 | 8/1999 | | |
| WO | 02/22784 A2 | 3/2002 | | |
| WO | 2010/150233 A2 | 12/2010 | | |
| WO | 2010/150235 A1 | 12/2010 | | |
| WO | WO 2010/150233 * | 12/2010 | ............. | C07K 14/47 |

OTHER PUBLICATIONS

Ye et al. (Modern Pathology, 20:375-383, 2007).*
Hofmeister et al. (Seminars in Cancer Biology, 13: 317-323, 2003).*
Carosella et al. (Trends in Immunology, 29(3): 125-132, 2008).*
European Search Report, dated Feb. 25, 2013 in corresponding European priority application.
Agaugue Sophie et al: "Role of HLA-G in tumor escape through expansion of myeloid-derived suppressor cells and cytokinic balance in favor of Th2 versus Th1/Th17", Blood, vol. 117, No. 26, Jun. 2011 (Jun. 2011), pp. 7021-7031.
Rouas-Freiss et al: "Expression of tolerogenic HLA-G molecules in cancer prevents antitumor responses", Seminars in Cancer Biology, Saunders Scientific Publications, Philadelphia, PA, US, vol. 17, No. 6, Nov. 9, 2007 (Nov. 9, 2007), pp. 413-421, XP022338887.
Van Lierop M J C et al: "Detection of HLA-G by a specific sandwich ELISA using monoclonal antibodies G233 and 56B.", Molecular Human Reproduction Aug. 2002, vol. 8, No. 8, Aug. 2002 (Aug. 2002), pp. 776-784, XP002692763.
Menier C et al: "Characterization of monoclonal antibodies recognizing HLA-G or HLA-E: New tools to analyze the expression of nonclassical HLA class I molecules", Human Immunology, New York, NY, US, vol. 64, No. 3, Mar. 1, 2003 (Mar. 1, 2003), pp. 315-326, XP002321005.
Paul Pascale et al: "HLA-G, -E, -F preworkshop: Tools and protocols for analysis of non-classical class I genes transcription and protein expression", Human Immunology, vol. 61, No. 11, Nov. 2000 (Nov. 2000), pp. 1177-1195, XP002692764.
Desai S A et al: "Structural relatedness of distinct determinants recognized by monoclonal antibody TP25.99 on beta 2-microglobulin-associated and beta 2-microglobulin-free HLA class I heavy chains.", Journal of Immunology (Baltimore, MD. 1950) Sep. 15, 2000, vol. 165, No. 6, Sep. 15, 2000 (Sep. 15, 2000), pp. 3275-3283, XP002692765.

(Continued)

*Primary Examiner* — Nelson B Moseley, II
(74) *Attorney, Agent, or Firm* — Young & Thompson

(57) ABSTRACT

An antibody or antigen-binding fragment thereof which specifically binds the α3 domain of a HLA-G protein, in particular binds the β2-microglobulin free HLA-G protein exhibiting an α3 domain. The nucleic acid molecules encoding a human HLA-G α3 domain polypeptide, which is selected from a group of specific sequences, and vectors for the cloning and/or expression of such nucleic acid molecules, recombined cells or cell lines and compositions for use in a host in need thereof to interfere with and neutralize the immune down-regulation due to HLA-G proteins, and/or improving or treating conditions showing HLA-G+ lesions, and/or improving or treating a neoplasic condition or disease. A method of producing the antibody or antigen-binding fragment thereof, immunogenic compositions for use to elicit in a host an immune response against the α3 domain of HLA-G protein, and an in vitro method for detecting HLA-G protein in a sample are also described.

18 Claims, 12 Drawing Sheets

(56) References Cited

OTHER PUBLICATIONS

Figure 1:
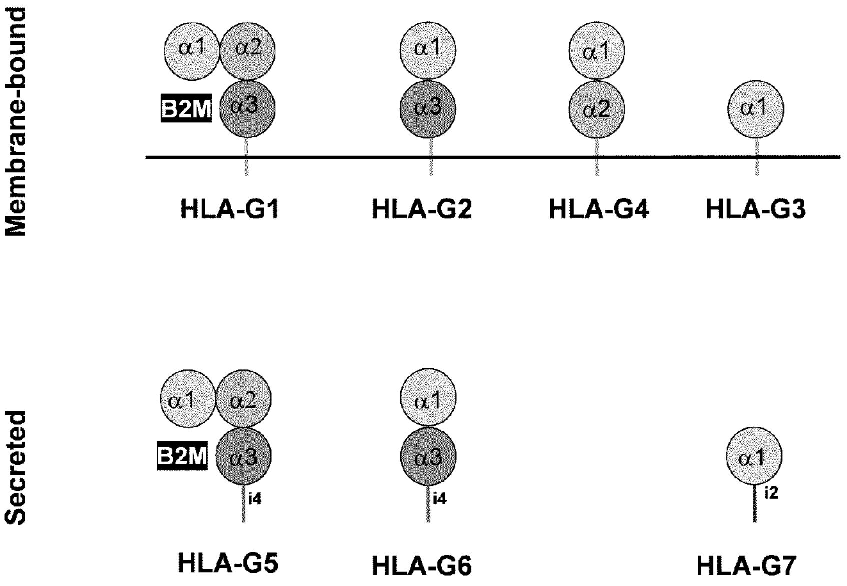

Tanabe M et al: "Structural and Functional Analysis of Monomorphic Determinants Recognized by Monoclonal Antibodies Reacting With the HLA Class Alpha-3 Domain", Journal of Immunology, vol. 148, No. 10, 1992, pp. 3202-3209, XP002692766.

Clements and McCluskey et al: "Crystal structure of HLA-G: A nonclassical MHC class / molecule expressed at the fetal-maternal interface" , PNAS, vol. 102, No. 9, 2005, pp. 3360-3365, XP003007722.

Lee N et al: "The membrane-bound and soluble forms of HLA-G bind identical sets of endogenous peptides but differ with respect to TAP association". Immunity 1995 US. vol. 3. No. 5. 1995. pp. 591-600. XP002720273.

Ye Shang-Rong et al: "Human leukocyte antigen G expression: as a significant prognostic indicator for patients with colorectal cancer". Modern Pathology. vol. 20. No. 3.; Mar. 2007 (Mar. 2007). pp. 375-383. XP002720274.

Lemaoult et al., "Synthetic HLA-G proteins for therapeutic use in transplantation", The FASEB Journal, vol. 27(9), Sep. 2013, pp. 3643-3651.

Tronik-Le Roux et al., "Novel landscape of HLA-G isoforms expressed in clear cell renal cell carcinoma patients", Molecular Oncology, 2017, pp. 1-18.

* cited by examiner

* Median survival = day at which 50% of grafts are rejected

Tumor volume according to the Human Melanoma concentration

Tumor volume according to the Human Melanoma concentration

SEQUENCE LISTING

```
<160> NUMBER OF SEQ ID NOS: 12

<210> SEQ ID NO 1
<211> LENGTH: 92
<212> TYPE: PRT
<213> ORGANISM: Artificial Sequence
<220> FEATURE:
<223> OTHER INFORMATION: HLA-Galpha3 protein sequence

<400> SEQUENCE: 1

Asp Pro Pro Lys Thr His Val Thr His His Pro Val Phe Asp Tyr Glu
1               5                   10                  15

Ala Thr Leu Arg Cys Trp Ala Leu Gly Phe Tyr Pro Ala Glu Ile Ile
            20                  25                  30

Leu Thr Trp Gln Arg Asp Gly Glu Asp Gln Thr Gln Asp Val Glu Leu
        35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80

His Glu Gly Leu Pro Glu Pro Leu Met Leu Arg Trp
                85                  90


<210> SEQ ID NO 2
<211> LENGTH: 108
<212> TYPE: PRT
<213> ORGANISM: Artificial Sequence
<220> FEATURE:
<223> OTHER INFORMATION: HLA-G ALPHA-3 domain used for protein
      immunization
<220> FEATURE:
<221> NAME/KEY: SITE
<222> LOCATION: (1)..(12)
<223> OTHER INFORMATION: linker sequence as found under SEQ ID NO 3
```

-continued

<400> SEQUENCE: 2

Gly Cys Gly Gly Gly Gly Ser Gly Gly Gly Gly Ser Arg Ala Asp Pro
1               5                   10                  15

Pro Lys Thr His Val Thr His His Pro Val Phe Asp Tyr Glu Ala Thr
            20                  25                  30

Leu Arg Cys Trp Ala Leu Gly Phe Tyr Pro Ala Glu Ile Ile Leu Thr
        35                  40                  45

Trp Gln Arg Asp Gly Glu Asp Gln Thr Gln Asp Val Glu Leu Val Glu
    50                  55                  60

Thr Arg Pro Ala Gly Asp Gly Thr Phe Gln Lys Trp Ala Ala Val Val
65                  70                  75                  80

Val Pro Ser Gly Glu Glu Gln Arg Tyr Thr Cys His Val Gln His Glu
                85                  90                  95

Gly Leu Pro Glu Pro Leu Met Leu Arg Trp Lys Gln
            100                 105

<210> SEQ ID NO 3
<211> LENGTH: 12
<212> TYPE: PRT
<213> ORGANISM: Artificial Sequence
<220> FEATURE:
<223> OTHER INFORMATION: Linker sequence

<400> SEQUENCE: 3

Gly Cys Gly Gly Gly Gly Ser Gly Gly Gly Gly Ser
1               5                   10

<210> SEQ ID NO 4
<211> LENGTH: 337
<212> TYPE: PRT
<213> ORGANISM: Homo sapiens
<220> FEATURE:
<221> NAME/KEY: MISC_FEATURE
<222> LOCATION: (1)..(337)
<223> OTHER INFORMATION: full HLA-G human protein as found under NM_002127.5

<400> SEQUENCE: 4

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Thr Leu Arg Gly Tyr Tyr Asn Gln Ser Glu
            100                 105                 110

Ala Ser Ser His Thr Leu Gln Trp Met Ile Gly Cys Asp Leu Gly Ser
        115                 120                 125

Asp Gly Arg Leu Leu Arg Gly Tyr Glu Gln Tyr Ala Tyr Asp Gly Lys
    130                 135                 140

Asp Tyr Leu Ala Leu Asn Glu Asp Leu Arg Ser Trp Thr Ala Ala Asp
145                 150                 155                 160

```
Thr Ala Ala Gln Ile Ser Lys Arg Lys Cys Glu Ala Ala Asn Val Ala
                165                 170                 175

Glu Gln Arg Arg Ala Tyr Leu Glu Gly Thr Cys Val Glu Trp Leu His
            180                 185                 190

Arg Tyr Leu Glu Asn Gly Lys Glu Met Leu Gln Arg Ala Asp Pro Pro
        195                 200                 205

Lys Thr His Val Thr His His Pro Val Phe Asp Tyr Glu Ala Thr Leu
    210                 215                 220

Arg Cys Trp Ala Leu Gly Phe Tyr Pro Ala Glu Ile Ile Leu Thr Trp
225                 230                 235                 240

Gln Arg Asp Gly Glu Asp Gln Thr Gln Asp Val Glu Leu Val Glu Thr
                245                 250                 255

Arg Pro Ala Gly Asp Gly Thr Phe Gln Lys Trp Ala Ala Val Val Val
            260                 265                 270

Pro Ser Gly Glu Glu Gln Arg Tyr Thr Cys His Val Gln His Glu Gly
        275                 280                 285

Leu Pro Glu Pro Leu Met Leu Arg Trp Lys Gln Ser Ser Leu Pro Thr
    290                 295                 300

Ile Pro Ile Met Gly Ile Val Ala Gly Leu Val Val Leu Ala Ala Val
305                 310                 315                 320

Val Thr Gly Ala Ala Val Ala Ala Val Leu Trp Arg Lys Lys Ser Ser
                325                 330                 335

Asp


<210> SEQ ID NO 5
<211> LENGTH: 1578
<212> TYPE: DNA
<213> ORGANISM: Homo sapiens
<220> FEATURE:
<221> NAME/KEY: source
<222> LOCATION: (1)..(1578)
<223> OTHER INFORMATION: full human HLA-G nucleic acid sequence as found
      under NM_002127.5

<400> SEQUENCE: 5

agtgtggtac tttgtcttga ggagatgtcc tggactcaca cggaaactta gggctacgga      60

atgaagttct cactcccatt aggtgacagg tttttagaga agccaatcag cgtcgccgcg     120

gtcctggttc taaagtcctc gctcacccac ccggactcat tctccccaga cgccaaggat     180

ggtggtcatg gcgccccgaa ccctcttcct gctgctctcg ggggccctga ccctgaccga     240

gacctgggcg ggctcccact ccatgaggta tttcagcgcc gccgtgtccc ggcccggccg     300

cggggagccc cgcttcatcg ccatgggcta cgtggacgac acgcagttcg tgcggttcga     360

cagcgactcg gcgtgtccga ggatggagcc gcgggcgccg tgggtggagc aggaggggcc     420

ggagtattgg gaagaggaga cacggaacac caaggcccac gcacagactg acagaatgaa     480

cctgcagacc ctgcgcggct actacaacca gagcgaggcc agttctcaca ccctccagtg     540

gatgattggc tgcgacctgg ggtccgacgg acgcctcctc cgcgggtatg aacagtatgc     600

ctacgatggc aaggattacc tcgccctgaa cgaggacctg cgctcctgga ccgcagcgga     660

cactgcggct cagatctcca agcgcaagtg tgaggcggcc aatgtggctg aacaaaggag     720

agcctacctg gagggcacgt gcgtggagtg gctccacaga tacctggaga acgggaagga     780

gatgctgcag cgcgcggacc cccccaagac acacgtgacc caccaccctg tctttgacta     840

tgaggccacc ctgaggtgct gggccctggg cttctaccct gcggagatca tactgacctg     900

gcagcgggat ggggaggacc agacccagga cgtggagctc gtggagacca ggcctgcagg     960
```

-continued

```
ggatggaacc ttccagaagt gggcagctgt ggtggtgcct tctggagagg agcagagata   1020

cacgtgccat gtgcagcatg aggggctgcc ggagcccctc atgctgagat ggaagcagtc   1080

ttccctgccc accatcccca tcatgggtat cgttgctggc ctggttgtcc ttgcagctgt   1140

agtcactgga gctgcggtcg ctgctgtgct gtggagaaag aagagctcag attgaaaagg   1200

agggagctac tctcaggctg caatgtgaaa cagctgccct gtgtgggact gagtggcaag   1260

tccctttgtg acttcaagaa ccctgactcc tctttgtgca gagaccagcc cacccctgtg   1320

cccaccatga ccctcttcct catgctgaac tgcattcctt ccccaatcac ctttcctgtt   1380

ccagaaaagg ggctgggatg tctccgtctc tgtctcaaat ttgtggtcca ctgagctata   1440

acttacttct gtattaaaat tagaatctga gtataaattt actttttcaa attatttcca   1500

agagagattg atgggttaat taaaggagaa gattcctgaa atttgagaga caaaataaat   1560

ggaagacatg agaacttt                                                 1578
```

<210> SEQ ID NO 6
<211> LENGTH: 546
<212> TYPE: DNA
<213> ORGANISM: Artificial Sequence
<220> FEATURE:
<223> OTHER INFORMATION: Nucleotide sequence used for DNA immunization
<220> FEATURE:
<221> NAME/KEY: misc_feature
<222> LOCATION: (1)..(6)
<223> OTHER INFORMATION: Restriction site
<220> FEATURE:
<221> NAME/KEY: misc_feature
<222> LOCATION: (7)..(15)
<223> OTHER INFORMATION: 5' kozak sequence (SEQ ID N?7)
<220> FEATURE:
<221> NAME/KEY: sig_peptide
<222> LOCATION: (13)..(84)
<223> OTHER INFORMATION: Signal peptide as found in Exon 1 of HLA-G
<220> FEATURE:
<221> NAME/KEY: misc_feature
<222> LOCATION: (85)..(87)
<223> OTHER INFORMATION: Nucleotides encoding Added amino acids
<220> FEATURE:
<221> NAME/KEY: misc_feature
<222> LOCATION: (88)..(93)
<223> OTHER INFORMATION: Nucleotides found at the end of the alpha 2 portion of HLA-G
<220> FEATURE:
<221> NAME/KEY: misc_feature
<222> LOCATION: (94)..(369)
<223> OTHER INFORMATION: Alpha 3 domain (SEQ ID NO 10)
<220> FEATURE:
<221> NAME/KEY: misc_feature
<222> LOCATION: (370)..(486)
<223> OTHER INFORMATION: Transmembrane-anchor protein encoding portion
<220> FEATURE:
<221> NAME/KEY: misc_feature
<222> LOCATION: (487)..(489)
<223> OTHER INFORMATION: nucleotides encoding added amino acids
<220> FEATURE:
<221> NAME/KEY: misc_feature
<222> LOCATION: (490)..(531)
<223> OTHER INFORMATION: V5-tag sequence
<220> FEATURE:
<221> NAME/KEY: misc_feature
<222> LOCATION: (532)..(540)
<223> OTHER INFORMATION: 3' stop codons (SEQ ID NO 8)
<220> FEATURE:
<221> NAME/KEY: misc_feature
<222> LOCATION: (541)..(546)
<223> OTHER INFORMATION: Restriction site

<400> SEQUENCE: 6

```
aagcttgccg ccatggtcgt tatggcaccc aggaccttgt tcctcctgct ctctggagca     60
```

ctgaccctta ctgagacatg ggccagtaga gccgaccccc ccaaaaccca tgtgacccac 120
cacccagtct ttgactatga agctacactg agatgttggg ccctgggctt ctaccccgca 180
gagatcatcc tgacctggca gcgcgacgga gaagatcaga cacaggacgt cgagctcgtg 240
gaaacccggc ctgctggtga tggcacattt cagaagtggg ccgccgtggt ggttccatcc 300
ggtgaggaac agcgctacac ttgccatgtg cagcacgagg gcttgcctga gcctcttatg 360
cttcggtgga agcagtcatc cctgccaact attcccatca tgggcattgt ggccggactg 420
gtggttctgg cagctgtggt gactggcgct gccgtcgccg ctgtcctctg gaggaaaaag 480
agcagcgatg gcaagccaat tcctaatcca ttgctgggcc tggactcaac ttgatgataa 540
ctcgag 546

<210> SEQ ID NO 7
<211> LENGTH: 9
<212> TYPE: DNA
<213> ORGANISM: Artificial Sequence
<220> FEATURE:
<223> OTHER INFORMATION: 5' kozak sequence

<400> SEQUENCE: 7 gccgccatg 9

<210> SEQ ID NO 8
<211> LENGTH: 9
<212> TYPE: DNA
<213> ORGANISM: Artificial Sequence
<220> FEATURE:
<223> OTHER INFORMATION: 3' stop codons

<400> SEQUENCE: 8 tgatgataa 9

<210> SEQ ID NO 9
<211> LENGTH: 276
<212> TYPE: DNA
<213> ORGANISM: Homo sapiens
<220> FEATURE:
<221> NAME/KEY: misc_feature
<222> LOCATION: (1)..(276)
<223> OTHER INFORMATION: nucleic acid sequence encoding a HLA-G ALPHA-3 domain polypeptide sequence as found in the sequence disclosed under accession number NM_002127.5, between positions 797 and 1072

<400> SEQUENCE: 9 gacccccca agacacacgt gacccaccac cctgtctttg actatgaggc caccctgagg 60
tgctgggccc tgggcttcta ccctgcggag atcatactga cctggcagcg ggatggggag 120
gaccagaccc aggacgtgga gctcgtggag accaggcctg caggggatgg aaccttccag 180
aagtgggcag ctgtggtggt gccttctgga gaggagcaga gatacacgtg ccatgtgcag 240
catgaggggc tgccggagcc cctcatgctg agatgg 276

<210> SEQ ID NO 10
<211> LENGTH: 276
<212> TYPE: DNA
<213> ORGANISM: Artificial Sequence
<220> FEATURE:
<223> OTHER INFORMATION: optimized nucleic acid sequence encoding for an HLA-G ALPHA-3 domain polypeptide sequence

<400> SEQUENCE: 10 gacccccca aaacccatgt gacccaccac ccagtctttg actatgaagc tacactgaga 60

-continued

```
tgttgggccc tgggcttcta ccccgcagag atcatcctga cctggcagcg cgacggagaa    120

gatcagacac aggacgtcga gctcgtggaa acccggcctg ctggtgatgg cacatttcag    180

aagtgggccg ccgtggtggt tccatccggt gaggaacagc gctacacttg ccatgtgcag    240

cacgagggct tgcctgagcc tcttatgctt cggtgg                              276


<210> SEQ ID NO 11
<211> LENGTH: 173
<212> TYPE: PRT
<213> ORGANISM: Artificial Sequence
<220> FEATURE:
<223> OTHER INFORMATION: Protein sequence encoded by the nucleic acid
      sequence SEQ ID NO 6
<220> FEATURE:
<221> NAME/KEY: SIGNAL
<222> LOCATION: (1)..(24)
<223> OTHER INFORMATION: Signal peptide as found in Exon 1 of HLA-G
<220> FEATURE:
<221> NAME/KEY: SITE
<222> LOCATION: (25)..(25)
<223> OTHER INFORMATION: Added amino-acid
<220> FEATURE:
<221> NAME/KEY: SITE
<222> LOCATION: (26)..(27)
<223> OTHER INFORMATION: Nucleotides found at the end of the Alpha2
      portion of HLA-G
<220> FEATURE:
<221> NAME/KEY: DOMAIN
<222> LOCATION: (28)..(119)
<223> OTHER INFORMATION: Alpha3 domain
<220> FEATURE:
<221> NAME/KEY: TRANSMEM
<222> LOCATION: (120)..(158)
<223> OTHER INFORMATION: Transmembrane-anchor protein encoding portion
<220> FEATURE:
<221> NAME/KEY: SITE
<222> LOCATION: (159)..(159)
<223> OTHER INFORMATION: Added amino-acid
<220> FEATURE:
<221> NAME/KEY: SITE
<222> LOCATION: (160)..(173)
<223> OTHER INFORMATION: V5-tag sequence

<400> SEQUENCE: 11

Met Val Val Met Ala Pro Arg Thr Leu Phe Leu Leu Leu Ser Gly Ala
1               5                   10                  15

Leu Thr Leu Thr Glu Thr Trp Ala Ser Arg Ala Asp Pro Pro Lys Thr
            20                  25                  30

His Val Thr His His Pro Val Phe Asp Tyr Glu Ala Thr Leu Arg Cys
        35                  40                  45

Trp Ala Leu Gly Phe Tyr Pro Ala Glu Ile Ile Leu Thr Trp Gln Arg
    50                  55                  60

Asp Gly Glu Asp Gln Thr Gln Asp Val Glu Leu Val Glu Thr Arg Pro
65                  70                  75                  80

Ala Gly Asp Gly Thr Phe Gln Lys Trp Ala Ala Val Val Val Pro Ser
                85                  90                  95

Gly Glu Glu Gln Arg Tyr Thr Cys His Val Gln His Glu Gly Leu Pro
            100                 105                 110

Glu Pro Leu Met Leu Arg Trp Lys Gln Ser Ser Leu Pro Thr Ile Pro
        115                 120                 125

Ile Met Gly Ile Val Ala Gly Leu Val Val Leu Ala Ala Val Val Thr
    130                 135                 140

Gly Ala Ala Val Ala Ala Val Leu Trp Arg Lys Lys Ser Ser Asp Gly
145                 150                 155                 160
```

-continued

```
Lys Pro Ile Pro Asn Pro Leu Leu Gly Leu Asp Ser Thr
                165                 170


<210> SEQ ID NO 12
<211> LENGTH: 108
<212> TYPE: PRT
<213> ORGANISM: Artificial Sequence
<220> FEATURE:
<223> OTHER INFORMATION: Sequence detailed in figure 5

<400> SEQUENCE: 12

Gly Cys Gly Gly Gly Gly Ser Gly Gly Gly Gly Ser Arg Ala Asp Pro
1               5                   10                  15

Pro Lys Thr His Val Thr His His Pro Val Phe Asp Tyr Glu Ala Thr
            20                  25                  30

Leu Arg Cys Trp Ala Leu Gly Phe Tyr Pro Ala Glu Ile Ile Leu Thr
        35                  40                  45

Trp Gln Arg Asp Gly Glu Asp Gln Thr Gln Asp Val Glu Leu Val Glu
    50                  55                  60

Thr Arg Pro Ala Gly Asp Gly Thr Phe Gln Lys Trp Ala Ala Val Val
65                  70                  75                  80

Val Pro Ser Gly Glu Glu Gln Arg Tyr Thr Cys His Val Gln His Glu
                85                  90                  95

Gly Leu Pro Glu Pro Leu Met Leu Arg Trp Lys Gln
            100                 105
```

ANTIBODIES AND FRAGMENTS THEREOF RAISED AGAINST THE ALPHA-3 DOMAIN OF HLA-G PROTEIN, METHODS AND MEANS FOR THEIR PREPARATION, AND USES THEREOF

The present invention relates to antibodies or antigen-binding fragments thereof directed against human leukocyte antigen-G (HLA-G) protein and raised against the α3 domain of HLA-G protein, especially, but not exclusively, when said α3 domain or its fragments are used to prepare said antibodies, under a monomeric and/or a dimeric form. The invention also relates to the use of such antibodies or fragments as defined herein in order to impact, advantageously to neutralize the immune down-regulation due to HLA-G proteins in a living body. Accordingly, the antibodies or fragments of the invention are suitable for use in order to remedy to a condition diagnosed in patient, when said condition takes advantage of a living body immune system down-regulation due to the presence of HLA-G proteins. Antibodies of the invention may also be used for diagnostic or monitoring a condition in a patient.

The invention thus provides means suitable for use in pathologies such as cancer or carcinogenic diseases as well as related or associated diseases or conditions, when these pathologies are associated with a tumour escape mechanism involving HLA-G proteins, notably within the context of immunotherapy treatments. More generally, the invention also provides means suitable for use in pathologies involving inappropriate expression of HLA-G proteins in a host.

The invention also provides means suitable as active agents for therapeutic application, especially means suitable for immunotherapeutic vaccination of mammals, in particular humans, in the same pathological context as described above. The invention relates in particular to means suitable for use in DNA vaccination protocol(s), in particular "naked DNA vaccine(s)".

The invention also provides means suitable for in vitro detecting HLA-G proteins or monitoring or diagnosing a health status or a pathologic condition, as well as means for monitoring or diagnosing a health status or pathologic condition, in particular a neoplasic condition, in a living body susceptible of presenting such a status or condition.

The invention also relates to methods for the preparation of the antibodies or fragments of the invention.

Class I antigens comprise classical antigens, HLA-A, HLA-B and HLA-C, which exhibit 3 globular domains ($\alpha_1$, $\alpha_2$ and $\alpha_3$) associated with β-2-microglobulin (B2M or β2M), as well as non-classical antigens HLA-E, HLA-F, and HLA-G.

HLA-G is a non-classical HLA class I molecule that was first identified in choriocarcinoma cells. In contrast to classical HLA class I molecules, HLA-G is characterized by limited polymorphism, presents a tissue-restricted expression, and differs as well by its expression, structure and functions. The eight exon gene spans 4.4 kb on chromosome 6 [1, 2]. Exons 2, 3 and 4 encode the $\alpha_1$, $\alpha_2$ and $\alpha_3$ extracellular domains respectively. The primary RNA transcript is alternatively spliced, resulting in the expression of seven isoforms, four of which are membrane-bound (HLA-G1, HLA-G2, HLA-G3 and HLA-G4), and three are soluble (HLA-G5, HLA-G6 and HLA-G7). HLA-G1 and HLA-G5 are the most abundant isoforms whose structures are typical of classical HLA class I molecule: a heavy chain of three globular domains non-covalently associated to β2M and a peptide, while the other isoforms are shorter, lacking one or two domains of the heavy chain, and do not bind β2M, as shown in FIG. 1.

HLA-G was initially described as being selectively expressed at the maternal-fetal interface on cytotrophoblast cells, depicted as a ligand for inhibitory receptors present on uterine natural killer (NK) cells, conferring protection to the semi-allogenic fetus by promoting maternal tolerance [3]. Besides being expressed in fetal tissues, HLA-G constitutive expression was later found in adult thymic medulla, cornea, pancreatic islets and erythroid and endothelial precursors cells. Furthermore, this molecule can also be neo-expressed in pathological conditions such as cancer, auto-immune, inflammatory diseases, viral infections or after allo-transplantation [4].

The immuno-inhibitory activity of HLA-G takes place through specific binding to three inhibitory receptors: leukocyte immunoglobulin-like receptor B1 (LILRB1/ILT2/CD85j), LILRB2 (ILT4/CD85d) and KIR2DL4 (or CD158d).

By linking these receptors, and unlike classical MHC class I molecules, HLA-G acts as a down-regulator of the immune system's main functions, and neither stimulatory functions nor responses directed against allogenic HLA-G have been reported to date. HLA-G was originally described as a tolerogenic molecule that inhibits uterine and peripheral blood NK cell cytolytic function, but it is known that the biological roles of HLA-G also comprise the inhibition of the cytolytic function of uterine and peripheral blood NK cells [5], the antigen-specific cytolytic function of cytotoxic T lymphocytes [6], the alloproliferative response of $CD4^+$ T cells [7, 8], the proliferation of T cells and peripheral blood NK cells [9-11], and the maturation and function of dendritic cells [12-14]. Furthermore, HLA-G is capable of inducing the generation of suppressive cells [12, 15-17].

HLA-G is capable of inhibiting all actors of the anti-tumoral responses, thus blocking all stages of immune responses. It is expressed in many types of primary tumors, metastases, and malignant effusions [18], summarized in FIG. 3, and it can also be found on tumor cells and tumor-infiltrating cells [19]. It was shown that HLA-G expression by tumor cell lines protects them from destruction by cytotoxic T lymphocytes and NK cells [20, 21]. Thus, the expression of HLA-G by malignant cells may prevent tumor immune elimination by locally inhibiting the activity of tumor infiltrating NK, cytotoxic T lymphocytes (CTL) and antigen presenting cells (APCs). The clinical relevance of HLA-G expression by tumors as a prominent immune escape mechanism was supported by the observation that HLA-G expression in B cell chronic leukaemia correlated with a strong immunodeficiency and poor clinical evolution [22]. Initially, HLA-G was proposed as a biomarker for diagnosis or prediction of the clinical outcomes in cancer. However, taking into account all the actors and stages of the anti-tumoral response where HLA-G is involved, it is conspicuous how vast the application of HLA-G in the therapeutic field against cancer could be.

Given that HLA-G expression is particularly relevant to the escape mechanisms of tumor cells by inhibiting effector cells, strategies to attain tumor cell rejection have been developed by neutralizing the immune down-regulation due to HLA-G, although they are not sufficient. Indeed, anti-HLA-G antibodies are rare, and only one blocking antibody exists (87G). This antibody only interacts with the $\alpha_1$ domain of the heavy chain of HLA-G associated to the β2M. Even though it has been described as capable of neutralizing HLA-G, and therefore restoring tumor rejection in vitro [21]

and in vivo [12, 15-17], its applicability is compromised as HLA-G is frequently expressed as a full length molecule not associated to β2M as well as β2M-free truncated isoforms. These isoforms can also bind the LILRB2 inhibitory receptor, therefore new antibodies of wider range of action should be developed. All other attempts at producing other blocking antibodies raised against the $\alpha_3$ domain of HLA-G have failed. Furthermore, HLA-G immunization has been remarkably inefficient yielding few specific antibodies. The reason for this has been recently elucidated. First, in kidney-transplanted patients, a negative association between sHLA-G and the presence of anti-allogenic HLA-G antibodies was demonstrated [23], indicating that the presence of HLA-G is antithetical to antibody production. Second, recent in vitro studies have confirmed that HLA-G/LILRB1 interaction impairs B-cell maturation and antibody production in humans [24]. Because HLA-G is known to exert a tolerogenic function through PIR-B in mice, which is expressed in murine B-cells and is functionally homologous to human LILRB1 and LILRB2, it is now clear that the HLA-G/PIR-B interaction leads to B-cell inhibition thus preventing antibody production in mice.

The invention therefore takes place in a context where actual production of anti-HLA-G blocking antibodies comes up against the problem that the generation of anti-HLA-G antibodies is extremely difficult because HLA-G is an immune-inhibitory molecule. The interaction of this molecule with receptors present on B cells and other immune cells leads, in the case of the former, to inhibition of maturation and antibody production. In other words, immunization with HLA-G is required to produce anti-HLA-G blocking antibodies, which in turn inhibits antibody production. For this reason, few HLA-G specific antibodies have been generated, of which 87G is the only existing blocking antibody. Therefore, the development of new immunization strategies to bypass this inhibition is crucial.

Thus, in order to break the above-mentioned vicious cycle and attain anti-HLA-G antibody production, the inventors have reasoned that the most challenging issue was to avoid the inhibition of B cell maturation. A further identified issue was to generate antibodies specific not only for β2M-associated HLA-G isoforms, but also for β2M-free and truncated isoforms, which are known to be produced and tolerogenic in humans [25-27] and in mice [28, 29].

Therefore, it is a purpose of the invention to produce specific anti-HLA-G antibodies while avoiding the inhibition of B cell maturation.

Having in mind to overcome HLA-G-mediated inhibition of antibody production, the inventors have first performed a series of investigations aimed at determining which HLA-G domain was responsible for the HLA-G inhibitory function. Studies have demonstrated that in mice, the α1 (alpha1) domain causes B cell inhibition. Indeed, protein constructs made up of the $\alpha_1\alpha_2\alpha_3$ domains, or $\alpha_1\alpha_3$ domains, or the $\alpha_1$ domain alone were tolerogenic in vivo in mice [28, 29]. This result is in line with previous studies that proved that the $\alpha_1$ domain of HLA-G is functional. Accordingly, the $\alpha_1$ domain of HLA-G is the target of most HLA-G antibodies.

Focusing more particularly on KIR2DL4 receptors, it was already known that its expression is mainly restricted to decidual NK cells [30]. KIR2DL4 is a specific receptor for HLA-G, for which it is the sole known ligand [31]. KIR2DL4 docks with the $\alpha_1$ domain of HLA-G, and more specifically, via residues Met76 and Gln79 which are characteristic of HLA-G [32]. It was further shown that these two residues are crucial to the inhibitory function of HLA-G and that their mutation prevented the inhibition of cytolytic activity of KIR2DL4-expressing NK cells by HLA-G in vitro. In spite of its specificity for HLA-G, KIR2DL4 is not likely to play a significant role in HLA-G inhibitory function except during pregnancy, mainly because its expression is restricted to decidual NK cells, and because in vitro and in vivo, it was shown that LILRBs played the key role through interaction with HLA-G $\alpha_3$ domain. It is possible, although unknown, that the $\alpha_1$ domain of HLA-G plays a direct role in the function of HLA-G, through KIR2DL4 or another, as yet unknown receptor.

It was however found out (publication submitted) that monomers or even dimers of the HLA-G $\alpha_3$ domain were, surprisingly, not tolerogenic in vivo, by contrast to the erroneous teaching disclosed in PCT/IB2010/052917 (FIG. 4, WO 2010/150233), in which carried out experiments were performed exclusively in vitro.

WO 2010/150233 indeed discloses polypeptides that could allegedly be used as tolerogenic agents, i.e. capable of mimicking HLA-G full function.

Figure 2:
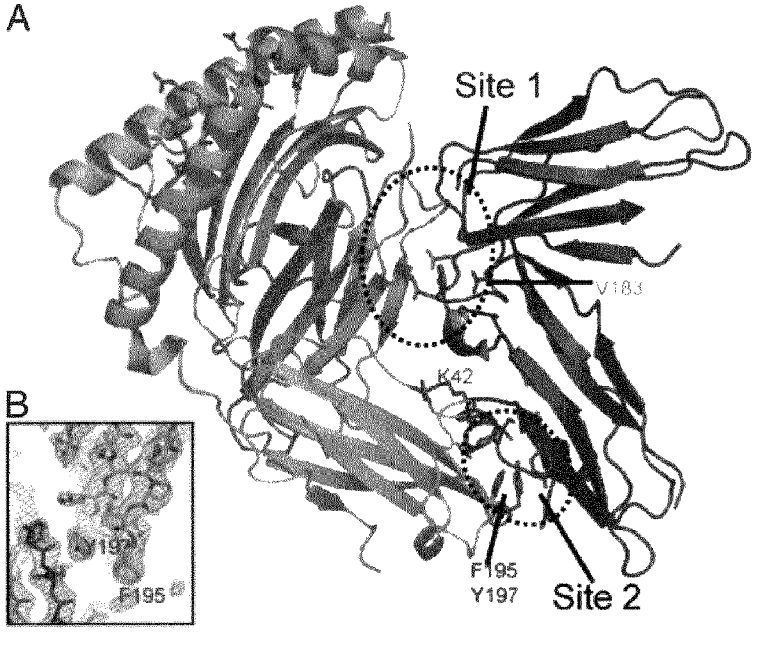

Like for other HLA Class I molecules, the recognition site for LILRB receptors is localized within the $\alpha_3$ domain of HLA-G [33-35]. LILRB1 is expressed on B cells, some T cells, some NK cells, and all monocytes and dendritic cells, whereas LILRB2 is myeloid-specific and only expressed by monocytes and dendritic cells [36]. LILRB1 and LILRB2 have been shown to bind a wide range of classical HLA molecules through the $\alpha_3$ domain when associated with β2M. HLA-G is the ligand of highest affinity for LILRB2 [37]. This stronger LILRB-binding capacity of HLA-G compared to other HLA Class I molecules is particularly well illustrated by the fact that HLA-G at the surface of tumor cells, but not classical HLA class I molecules, is capable of engaging the LILRB1 and/or LILRB2 receptors of cytolytic effectors with sufficient strength to block the function of these effectors and thus protect the tumor cells from immune destruction [38]. LILRB1 and LILRB2 do not bind the same HLA-G structures [39]. In addition, it has been demonstrated that they present higher affinity for HLA-G multimers than monomeric structures [37]. It is important to highlight the difference between the way LILRB1 and LILRB2 bind to their ligands: LILRB1 recognizes only β2M-associated HLA-G structures, whereas LILRB2 recognizes both β2M-associated and β2M-free HLA-G full length heavy chains [40, 41] as well as truncated $\alpha_1$-$\alpha_3$ domain isoforms (HLA-G2/G6) [29, 39]. Indeed, LILRB2 shows remarkably distinct HLA-binding recognition by binding preferentially the $\alpha_3$ domain than β2M, involving the aromatic amino acids Phe195 and Tyr197, as shown in FIG. 2. This explains the β2M independent HLA-G binding of the latter receptor and its high affinity for β2M-free isoforms.

Therefore, evidence available to date may suggest a tolerogenic function of HLA-G that is mediated mainly by the interaction of its $\alpha_3$ domain with LILRB1 and LILRB2 molecules.

However, it was additionally demonstrated that the $\alpha_3$ domain is not inhibitory with respect to the immune response while containing the recognition site for LILRB1 and LILRB2 receptors. Indeed, it was surprisingly found, and then assessed, that the sole presence of an HLA-G $\alpha_3$ domain is not sufficient to initiate the tolerogenic function of HLA-G.

It was also concluded that the binding of HLA-G dimers to LILRB1 and LILRB2 molecules is highly dependent on the unique HLA-G $\alpha_3$ domain, although β2M is required for HLA-G/LILRB1 binding. These findings revealed that the HLA-G $\alpha_3$ domain, as it appears to be non tolerogenic in itself, is likely to be a target of choice to work on the tolerogenic function of HLA-G protein.

By "not tolerogenic", it is meant herein that the above-mentioned monomers or even dimers of the HLA-G $\alpha_3$ domain are not capable of mimicking HLA-G function in down-regulation of the immune response when administered to a living organism, in particular a mammal. According to a particular embodiment, the tolerogenicity or the absence of tolerogenicity is appreciated taking into account the activity of at least one among a broad spectrum of agents generally involved in immune responses, such as B cells, T cells, NK cells, and monocytes or dendritic cells, cited as examples only.

For the purpose of the invention, tolerogenicity is in particular determined through the capacity of the assayed molecule (e.g. the α3 domain of HLA-G) to inhibit B cell maturation in vivo and, as a result, effective production of anti-HLAG antibodies.

It is also known, in particular from DESAI S. et al. in "*Structural relatedness of distinct determinants recognized by monoclonal antibody TP*25.99 *on beta* 2-*microglobulin-associated and beta* 2-*microglobulin-free HLA class I heavy chains*" (Journal of Immunology 15 Sep. 2000, vol. 165, no. 6, pages 3275-3283) the so-called monoclonal antibody TP25.99, which binds to a determinant expressed on the $\alpha_3$ domain of all HLA-A, -B and -C proteins. However, as stated in PAUL PASCALE et al. in "HLA-G, -E, -F preworkshop: Tools and protocols for analysis of non-classical class I genes transcription and protein expression" (HUMAN IMMUNOLOGY, vol. 61, no. 11, November 2000, pages 1177-1195), the antibody TP25.99 can be used to discriminate between HLA-G and other class I antigens, since the TP25.99 antibody recognizes HLA-A, HLA-B, HLA-C, and HLA-E antigens, but not HLA-G. It can be seen from the preceding that, albeit an antibody binding to a determinant expressed on the $\alpha_3$ domain of some Class I HLA antigens may exist, it has been confirmed by failure that obtaining an antibody binding to a determinant expressed on the $\alpha_3$ domain of HLA-G is non-trivial.

Accordingly, the invention concerns an antibody or an antigen-binding fragment thereof, which has been raised against the α3 domain of HLA-G protein, when the $\alpha_3$ domain is used as an immunogen or, more efficiently when the DNA molecule encoding the $\alpha_3$ domain of HLA-G protein is used for immunisation. The invention also concerns methods for obtaining such an antibody or an antigen-binding fragment thereof, in particular an antibody or an antigen-binding fragment thereof having a particular tridimensional conformation (also referred to as "recognizing a conformational epitope in the α3 domain of HLA-G protein" herein).

As a result, the present invention relates to an antibody or an antigen-binding fragment thereof which specifically binds the α3 domain of HLA-G protein.

In a particular embodiment, an "α3 domain of HLA-G protein" is defined as domain having a polypeptide sequence as disclosed under SEQ ID No1.

Optionally, in a particular embodiment, an "α3 domain of HLA-G protein" is defined as domain having a polypeptide sequence as disclosed under SEQ ID No1 and further having the two amino-acid residues RA at the N-terminal extremity of SEQ ID No1, and/or the two amino-acid residues KQ at the C-terminal extremity of SEQ ID No1.

In a specific embodiment, the present invention relates to an antibody or an antigen-binding fragment thereof which specifically binds the α3 domain of HLA-G protein having a conformation as naturally found in cells expressing HLA-G. In other words, such an antibody or antigen-binding fragment thereof of the invention recognizes a specific conformational epitope of the α3 domain of HLA-G as naturally found in cells expressing HLA-G.

HLA-G protein can be found under several structural (or tridimensional) forms, which are commonly called isoforms. Examples of HLA-G protein isoforms are given in FIG. 1. HLA-G1 and HLA-G5 are respectively membrane-bound or secreted HLA-G proteins that are typically found associated with β2-microglobulin protein. By contrast, HLA-G2, HLA-G3 and HLA-G4 are membrane-bound HLA-G protein isoforms not exhibiting concomitantly all of the, α2 and α3 domains. HLA-G6 and HLA-G7 are secreted HLA-G protein isoforms also not exhibiting concomitantly all of the α2 and α3 domains.

Within the context of the present invention, "HLA-G protein binding" by antibodies or antigen-binding fragments of the invention means that the antibodies or antigen-binding fragments of the invention recognize HLA-G protein isoforms exhibiting α3 domain or found associated with an α3 domain, while being further found associated or not associated with β2-microglobulin protein or fragment thereof.

By "associated", it is meant a close interaction between the considered domains or domains and proteins. Such an interaction can be achieved by the formation of hydrogen bonds, or van der Waals interactions, or ionic bonds.

By "recognize", it is meant that a specific recognition occurs that enables binding.

The β2-microglobulin protein which, in some cases, can be found associated to HLA-G protein, is however not systematically present in all isoforms of the HLA-G protein. As detailed above, the presence of an associated β2-microglobulin protein is also not necessary to enable the binding of an HLA-G protein to the LILRB2 inhibitory receptor.

Within the context of the invention, "β2-microglobulin free HLA-G protein" therefore relates to HLA-G protein that is not associated with β2-microglobulin protein. By "β2-microglobulin free truncated HLA-G protein isoform" or "β2-microglobulin free truncated HLA-G protein isoform exhibiting an α3 domain", reference is made to an HLA-G protein not exhibiting all the domains that may be found in an HLA-G protein, and not associated with β2-microglobulin protein.

In a particular embodiment of the invention, the antibodies or antigen-binding fragments thereof specifically binds the α3 domain when present in HLA-G, in particular in β2-microglobulin free HLA-G, i.e., the β2-microglobulin free HLA-G exhibiting an α3 domain or the β2-microglobulin free truncated HLA-G exhibiting an α3 domain.

By "bind" or "binding" as used herein, it is made reference to an antigen-antibody type interaction. By "specific binding" properties of the antibodies or antigen-binding fragments thereof it is meant that the antibodies or antigen-binding fragments thereof directly bind to the α3 domain of HLA-G protein to the exclusion of other domains of the HLA-G protein or to the exclusion of binding to other human proteins, in particular to the exclusion of binding to other HLA proteins. The binding capacity may be measured by determination of the binding affinity for the α3 domain of HLA-G protein, according to conventional tests known in the art of the invention, in particular the binding affinity can be assayed by ELISA, or Western Blot analysis. According to a specific embodiment, "specific binding" means that the interaction between the antibodies or antigen-binding fragments of the invention and the α3 domain of HLA-G protein through such a specific binding is more stable than interaction between the antibodies or antigen-binding fragments of the invention and other human proteins, or other HLA-G domains or other HLA proteins. Stability can be appreciated by comparing the persistence over time, or under competition conditions, of the antigen-antibody complex and, in particular, by measuring the dissociation constant of the antibodies recognizing the α3 domain of the HLA-G protein.

It is a purpose of the invention to produce specific anti-HLA-G antibodies for the HLA-G isoforms encompassing an α3 domain, or recognizing HLA-G isoforms associated with an α3 domain.

Accordingly, when referring to binding to a HLA-G protein, the invention especially relates to binding to a HLA-G isoform that exhibits an α3 domain.

According to a particular embodiment, the α3 domain of HLA-G protein referred to herein is as found in non-pathological human cells. Such an α3 domain of HLA-G protein is disclosed in the literature and databases available to one skilled in the art of the invention. The α3 domain of HLA-G protein is in particular annotated in entry NM_002127 (NCBI access number version NM_002127.5). Without prejudice to the above and according to a particular embodiment, said domain is defined as the domain having a polypeptide sequence as disclosed under SEQ ID No1.

By "antigen-binding fragment" of an antibody of the invention, it is meant a part of an antibody, i.e. a molecule corresponding to a portion of the structure of the antibody of the invention that exhibits antigen-binding capacity for the α3 domain of HLA-G protein. In a particular embodiment, said fragment exhibits substantially the same antigen-binding capacity for said domain as the antigen-binding capacity of the antibody having a full antibody structure. The antigen-binding capacity can be determined by measuring the affinity of the antibody and of the considered antigen-binding fragment to the targeted antigen.

Antigen-binding fragments of antibodies encompass fragments which comprise the hypervariable domains designated CDRs (Complementary Determining Regions) or part(s) thereof encompassing the recognition site for the antigen, i.e., the α3 domain of the HLA-G protein, thereby defining antigen recognition specificity. Each Light and Heavy chain (respectively VL and VH) of a four-chain immunoglobulin has three CDRs, designated VL-CDR1, VL-CDR2, VL-CDR3 and VH-CDR1, VH-CDR2, VH-CDR3, respectively. Thus the invention relates to fragments of antibodies of the invention (antigen-binding fragments), which comprise or consist in all or a selection of CDRs among VL-CDR1, VL-CDR2, VL-CDR3 and VH-CDR1, VH-CDR2 and VH-CDR3 or functional portions thereof, i.e. portions that exhibit the desired binding capacity, preferably with a high affinity, for the α3 domain of HLA-G protein.

Fragments that comprise or consist in VH-CDR3 and/or VL-CDR3 or functional portions thereof are especially preferred when CDR3 regions appear to be determinant in antigen recognition specificity. Particular antigen-binding fragments comprise CDR1, CDR2 and CDR3 domains of a VH and/or a VL of an antibody.

For illustration purpose of specific embodiments of the invention, antigen-binding fragments of an antibody that contain the variable domains comprising the CDRs of said antibody encompass Fv, dsFv, scFv, Fab, Fab', F(ab')2 which are well defined with reference to Kabat and also Roitt I. et al (Fundamental and Applied Immunology MEDSI/McGraw-Hill). Fv fragments consist of the VL and VH domains of an antibody associated together by hydrophobic interactions; in dsFv fragments, the VH:VL heterodimer is stabilised by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen-binding sites, like the native immunoglobulin molecule; on the other hand, Fv (a VH-VL dimmer constituting the variable part of Fab), dsFv, scFv, Fab, and Fab' fragments are monovalent, i.e. they comprise a single antigen-binding site.

These basic antigen-binding fragments of the invention can be combined together to obtain multivalent antigen-binding fragments, such as diabodies, tribodies or tetrabodies. These multivalent antigen-binding fragments are also part of the present invention.

For illustration purposes, the antibodies or fragments thereof of the invention may be obtained through immunization of a mammal, in particular a rodent, especially mice or rats, with a monomeric or dimeric α3 domain of HLA-G protein. As further exemplified herein, the inventors have demonstrated that immunization of both Balb/c and C57Bl mice enabled the production of antibodies according to the present invention. It can be concluded that various mammal genotypes are suitable for implementing the present invention through immunization of a mammal.

According to a particular, non-exclusive embodiment, the antibodies or fragments thereof of the invention are obtained following immunization of an animal chosen among a mammal suitable for preparation of antibodies to be recovered, in particular a rodent, especially mice or rats, with a monomeric α3 domain of HLA-G protein. Immunization protocol may encompass priming and boosting steps.

Immunization methods are numerous and conventional in the art of the invention and depends on the final purpose of elicited antibodies, whether recovered or acting as an active ingredient in vivo.

According to particular results achieved with currently available techniques of antibody generation, some immunization methods may however not be appropriate for efficient and reliable production of antibodies of the invention, i.e., may be disregarded with respect to other methods for further recovering the antibodies of the invention as illustrated in the examples and by the failure to obtain antibodies in the prior art.

According to a particular embodiment, particular mammal genotypes, which are suitable for implementing the present invention through immunization of a mammal may be chosen so as to enable production of antibodies or fragments thereof of the invention at an industrial scale, in particular as exemplified herein.

According to a particular embodiment, the antibodies or fragments thereof of the invention are obtained following a DNA immunization protocol, in particular an immunization protocol involving immunization of an animal chosen among a non-human mammal suitable for preparation of antibodies to be recovered, as discussed above, in particular a rodent, especially mice or rats, with an appropriate vector or without vector, for DNA delivery, for example using a step of electroporation of DNA as further detailed below. Although DNA immunization protocol that may be used may encompass recourse to adjuvant(s), the invention also relates to a method of immunization involving "naked DNA" administration without adjuvant.

In another aspect, the invention also relates to the use of a DNA in an immunization protocol for in vivo eliciting antibodies of the invention, in a mammal, especially a human, for therapeutic purpose. In such a case, the invention relates the DNA encoding the α3 domain of the HLA-G protein for use as a drug for the elicitation of antibodies against the α3 domain of the HLA-G protein is expressed in vivo by the immunized host, for treating the host, especially the human host subjected to the DNA immunization protocol, according to the definitions provided herein. In this context, is also encompassed a method of immunization involving "naked DNA" administration, for said therapeutic purpose.

In a specific embodiment of the invention, antibodies or antigen-binding fragments of the invention bind the α3 domain of HLA-G protein when this domain is under a monomeric or dimeric form. By "dimeric form" it is meant an assembly of two human HLA-G α3 domains or fragments thereof. However, the present invention also encompasses the binding of the α3 domain of HLA-G protein when this domain is found under a multimeric form or engaged in a multimeric assembly, i.e. involving other domains than α3 or more than two α3 domains or fragments thereof.

As stated above, HLA-G protein may be found associated with β2-microglobulin protein.

Accordingly, in a particular embodiment, an antibody or an antigen-binding fragment thereof of the invention binds the α3 domain when present in a HLA-G protein, in particular binds the β2-microglobulin free HLA-G protein exhibiting an α3 domain or a β2-microglobulin free truncated HLA-G protein isoform exhibiting an α3 domain.

According to a particular embodiment, an antibody or an antigen-binding fragment thereof of the invention both binds the α3 domain of a HLA-G protein when said domain is under a monomeric and/or a dimeric form, and binds the α3 domain when present in a HLA-G protein, in particular binds the β2-microglobulin free HLA-G protein exhibiting an α3 domain or a β2-microglobulin.

In a preferred embodiment, an antibody or an antigen-binding fragment thereof of the invention binds at least one or several of the HLA-G protein isoforms selected amongst: HLA-G1, HLA-G2, HLA-G5 and HLA-G6.

In a particular embodiment, an antibody or an antigen-binding fragment thereof of the invention binds HLA-G1.

In a particular embodiment, an antibody or an antigen-binding fragment thereof of the invention binds HLA-G5.

In a particular embodiment of the invention, antibodies or antigen-binding fragments of the invention are blocking antibodies or blocking antigen-binding fragments thereof.

By "blocking", it is meant that binding between HLA-G proteins exhibiting an α3 domain, or associated with an α3 domain, as defined herein, and their receptors recognized by the α3 domain, is prevented or strongly diminished in the presence of antibodies or antigen-binding fragments of the invention. Therefore, by "blocking", it is meant that the biological function subsequent to binding between HLA-G proteins through an α3 domain and their receptors is abolished or strongly diminished in the presence of antibodies or antigen-binding fragments of the invention. The biological function referred to in this context is the immuno-inhibitory activity of HLA-G proteins exhibiting an α3 domain, as disclosed herein and assessed in the literature. Accordingly, it can be said that the antibodies or antigen-binding fragments of the invention are antagonist agents of HLA-G protein, or antagonist agents of the effect(s) of HLA-G protein having and α3 domain, because interfering with the activity of such HLA-G protein and/or opposing to its activity at least in part or completely, directly or indirectly.

According to a particular embodiment, binding between at least one or several of the following HLA-G protein isoforms: HLA-G1, HLA-G2, HLA-G5 or HLA-G6 and their receptors recognized by the α3 domain is prevented.

In a specific embodiment, an antibody or an antigen-binding fragment thereof of the invention blocks the binding of a HLA-G protein exhibiting an α3 domain to at least one of LILRB1 or LILRB2 receptors, in particular blocks the binding of said HLA-G protein to both LILRB1 and LILRB2 receptors.

In a particular embodiment of the invention, antibodies or antigen-binding fragments of the invention recognize a linear or a conformational epitope contained in either:

a. an amino-acid sequence having SEQ ID No1,
b. an amino-acid sequence having at least 85%, preferably at least 90%, more preferably at least 95%, and most preferably at least 98% or 99% identity over its whole length with the amino-acid sequence having SEQ ID No1.

Such an epitope may also be contained in an amino-acid sequence encoded by a polynucleotide sequence comprising or consisting of the nucleotidic sequence of SEQ ID No 9 or SEQ ID No 10 or SEQ ID No6, or an amino-acid sequence encoded by a polynucleotide sequence having at least 80 to 85%, preferably at least 90%, more preferably at least 95%, and most preferably at least 98% or 99% identity over their whole length with one of the polynucleotides having the sequence of SEQ ID No 9 or SEQ ID No 10 or SEQ ID No6.

The term "epitope" is used herein as a synonym for "antigenic determinant", as found on an antigen, for the purpose of defining the site to which the antibodies or fragments of the invention bind through their paratope. Within the context of the invention, an epitope contains at least 5 amino-acid residues, in particular at least 8 amino-acid residues.

By "linear (or sequential, continuous) epitope" it is meant an epitope consisting of amino-acid residues that form a sequence together in the primary sequence of the protein antigen, i.e. the α3 domain of HLA-G protein.

By "conformational (or assembled, discontinuous) epitope" it is meant an epitope consisting of amino-acid residues, at least some of which being separated from the others in the primary sequence of the protein antigen, i.e. the α3 domain of HLA-G protein, and which together assemble in a 3D-structure that is recognized by an antibody.

In a particular embodiment of the invention, antibodies or antigen-binding fragments thereof are provided as a polyclonal serum or are purified from a polyclonal serum, for example as described in the Results section of the present disclosure.

The invention also relates to a polyclonal serum comprising antibodies of the invention as disclosed herein.

By "polyclonal serum" it is meant a serum comprising an heterogeneous population of many different antibodies or fragments thereof raised against a specific antigen, which are therefore specific for a number of distinct antigenic determinants found on said specific antigen.

In a particular embodiment of the invention, antibodies of the invention are monoclonal antibodies or are chimeric monoclonal antibodies.

The invention therefore also relates to monoclonal antibodies, meaning that a composition of these antibodies comprises antibodies that are identical, in terms of antigen-binding specificity and, accordingly, in terms of variable region composition. Hence the antibodies may qualify as monoclonal even if they are obtained by techniques alternative to the technique of hybridoma, as known in the art of the invention.

In another embodiment, the invention also relates to a chimeric molecule which comprises an antibody according to any of the definition provided herein or a antigen-binding fragment thereof, wherein said antibody or antigen-binding fragment thereof is associated with a functionally different molecule.

A chimeric molecule of the invention may be either a fusion chimeric protein or a conjugate resulting from any suitable form of attachment including covalent attachment, grafting, chemical bonding with a chemical or biological group or a molecule, such as a protective group or a molecule suitable for protection against proteases cleavage in vivo, for improvement of stability and/or half-life of the antibody or antigen-binding fragment, with a biologically active molecule, especially a therapeutic active ingredient, a vector (including especially a protein vector) suitable for targeting the antibody or antigen-binding fragment to specific cells or tissues of the human body, or with a label or with a linker, especially when fragments of the antibody are used.

The invention also relates to a nucleic acid molecule encoding an antibody or an antigen-binding fragment thereof of the invention, as disclosed herein.

The invention also concerns a nucleic acid molecule encoding a human HLA-G α3 domain polypeptide, which is selected from the group consisting of:

a. a polynucleotide derived from the nucleotide sequence of SEQ ID No9 and having from 250 to 305 nucleotides in length, or;
b. a polynucleotide comprising or consisting of the nucleotide sequence of SEQ ID No 10 or SEQ ID No6 and having from 250 to 550 nucleotides in length, or;
c. a polynucleotide having at least 80%, preferably at least 85%, more preferably at least 90% or 95%, and most preferably at least 98% or 99% identity over their whole length with one of the polynucleotides having the sequence of SEQ ID No 9 or SEQ ID No 10 or SEQ ID No6 and having from 250 to 550 nucleotides in length, in particular a polynucleotide which encodes the polypeptide α3 having the sequence of SEQ ID NO:1, or;
d. a polynucleotide which is a fragment of the polynucleotide of a. or b. or c. and having from 30 to 150 nucleotides in length;

to the exclusion of a nucleic acid molecule comprising or consisting of the nucleotide sequence of SEQ ID No9, as such.

By "derived", it is in particular meant that a nucleic acid molecule of the invention is an optimized sequence with respect to the natural HLA-G polynucleotidic sequence, in particular as disclosed in databases. The invention does not encompass a nucleic acid molecule having the natural HLA-G polynucleotidic sequence, as particularly disclosed in SEQ ID No9 as such.

Accordingly, polynucleotides of the invention can be optimized sequences, the codons of which have been in part substituted for more frequent codons determined with respect to the cells used for the expression of the polynucleotide. Cells used for the expression of the polynucleotide can be mammal cells, in particular human cells, or eukaryotic cells such as insect or plant cells, or prokaryotic cells. Polynucleotide of SEQ ID No6 illustrates such an optimized molecule. Optimisation techniques in this field are conventional.

Because of the degeneracy of the genetic code, silent substitutions are possible, especially at the level of the third position of a codon, which is known to be a particularly labile position. Therefore, an optimized sequence may present 25% or 30% and up to 40% or 45% modified nucleotides by comparison with the nucleotides present at a given position in the natural HLA-G polynucleotidic sequence. In other words, an optimized sequence may have respectively 75% or 70% to 60% or 55% similarity by comparison with the natural HLA-G polynucleotidic sequence, in particular as disclosed in databases.

It can be seen herein that DNA immunization experiments were performed using a plasmid comprising SEQ ID No6, which is an optimized nucleic acid sequence encoding the α3 HLA-G domain as disclosed under SEQ ID No1: the optimization rule set used led to an optimized nucleic sequence (disclosed under SEQ ID No10) encoding the α3 HLA-G domain that has about 83.4% identity with the corresponding natural nucleic acid sequence (disclosed under SEQ ID No9 herein). Therefore, the present invention encompasses polynucleotides having at least 80%, in particular 81, 82, 83 or 84%, preferably at least 85%, more preferably at least 90% or 95%, and most preferably at least 98% or 99% identity over their whole length with one of the polynucleotides having the sequence of SEQ ID No 9 or SEQ ID No 10 or SEQ ID No6.

According to a particular embodiment, an optimized nucleic acid sequence as defined herein encodes a polypeptide consisting in an α3 polypeptide or having an α3 portion, in particular a polypeptide having the sequence of SEQ ID NO:1.

For the purpose of recovery of the antibodies of the invention from producing cells the polynucleotide may comprise, upstream from the nucleotide sequence encoding the antibody chains, a sequence encoding a signal peptide for secretion of the expressed antibody. They may also comprise, downstream from the nucleotide sequence encoding the antibody chains, a sequence encoding a transmembrane anchor.

Accordingly, SEQ ID No 10 discloses the optimized nucleotidic sequence of human HLA-G restricted to the sequence encoding the α3 domain of human HLA-G as used in the plasmid described in the Results section herein, suitable for use for preparation of antibodies of the invention.

SEQ ID No 9 also discloses a nucleotidic sequence derived from human HLA-G and restricted to the sequence encoding the α3 domain of human HLA-G, suitable for use for preparation of antibodies of the invention, as disclosed in exon 4 of HLA-G protein found under NCBI accession number NM_002127.5, between positions 797 and 1072.

SEQ ID No 6 discloses the nucleotidic sequence used for the DNA immunization experiment described in the Results section herein, i.e, an optimized nucleotidic sequence encoding a HLAG signal peptide, the α3 domain of human HLA-G, a HLA-G transmembrane spanning sequence fused to the simian virus 5 V5 protein tag sequence, with a 5' Kozak initiation sequence and a 3' pair of stop condons, and HindIII and XhoI restriction sites.

Polynucleotide fragments as mentioned above have advantageously a sequence of at least 30 nucleotides and are shorter than their sequence of origin.

According to a particular embodiment, polynucleotides of the invention may also comprise one or more sequence(s)

encoding one or more marker peptide(s) for detecting, and/or facilitating the purification of, said protein.

The invention also concerns a vector for the cloning and/or for the expression of a polynucleotide disclosed herein, especially a plasmid suitable for cloning and/or expressing in mammalian cells, especially a murine cell or a cell line. According to a particular embodiment, regulation sequences for transcription and expression may be added. According to a particular embodiment, the invention also concerns a vector suitable for DNA immunization, as detailed below.

The invention further relates to cells or cell lines recombined with a polynucleotide of the invention, especially a mammalian cell, especially a murine cell or a cell line.

According to a particular aspect, the polynucleotides and vectors of the invention as disclosed herein are suitable for the implementation of a DNA immunisation protocol (also referred to as DNA vaccination herein) on a mammal, in particular a human or a rodent. Such a protocol can be used for the purpose of producing antibodies (especially when the host is not a human), or for therapeutic purposes, as further detailed below.

By “DNA immunization” or “DNA vaccination”, it is made reference to the technique of direct administration into the cells of a living host of a genetically engineered nucleic acid molecule encoding at least an antigen portion (also referred to as nucleic acid vaccine or DNA vaccine herein) to produce an immunological response in said cells. DNA vaccines are known as third generation vaccines, and have the particularity to use the host cellular machinery for expressing peptide(s) corresponding to the administered nucleic acid molecule and/or achieving the expected effect, in particular antigen expression at the cellular level, and furthermore immunotherapeutic effect(s) at the cellular level or within the host organism.

To this end, the administered nucleic acid molecule(s) are generally administered through means suitable for expression of said nucleic acid molecule(s) by the host’s transfected cell(s), and are generally borne by bacterial plasmids (or other vectors where appropriate) so that the coding nucleic acid is capable to enter the nucleus of the host’s transfected cell(s) so as to see the antigen portion(s) of the administered nucleic acid molecule(s) expressed to produce, at the cellular level, peptide(s) corresponding to said antigen portion(s). DNA vaccines generally have the potency to induce a wider range of immune response types within the organism(s) to which they are administered, and are known to impact the conformation of the peptide corresponding to the antigen portion(s) of the administered DNA vaccine.

Vectors (in particular plasmids) for DNA vaccine(s) contain at least one nucleic acid encoding an antigen portion, especially the α3 domain of the HLA-G protein according to the present invention. The construction of bacterial plasmids for DNA vaccine(s) is commonly known and accomplished using recombinant DNA techniques. Vectors (and in particular plasmids) for DNA vaccine(s) may require the presence of any one of the following features such as: (1) a promoter for optimal expression in mammalian cells, (2) a selection marker, (3) polyadenylation (polyA) sequences, (4) inclusion of intron sequence(s). The vector used can also be optimized for transcription in the host cell(s). Construction of vectors for DNA vaccines are known in the art. Reference is for example made to Petrovsky et al. (Expert Rev Vaccines, 2012 February; 11(2): 189-209), for further details.

Several delivery methods for DNA vaccines are commonly available, such as:

intramuscular (IM) or intradermal (ID) injection (by needle) of the DNA vaccine in saline solution, which delivers the DNA to the extracellular spaces. This method may be assisted by “electroporation”, which uses electrical stimulation of biological tissues to transiently permeabilize cell(s) membrane(s);

“gene-gun delivery”, which involves bombarding the skin with plasmid-coated gold particles by employing ballistic devices, which enables DNA delivery directly into cell(s) cytoplasm;

delivery through “needle-free delivery systems”, which enables spraying the plasmid DNA through the skin, for example trough a device such as the Biojector™ device;

“topical administration” in aqueous solution, in particular on mucosal tissues,

All these methods are commonly known by the skilled in the art in the field, and encompassed by the present invention. They can be suitably properly used within the context of the invention, according to the knowledge of the skilled in the art. Reference is made to Petrovsky et al. (Expert Rev Vaccines, 2012 February; 11(2): 189-209), for further details.

Adjuvants may be used when DNA immunization is performed. They may also help in modulating the immune response that is sought. Traditional adjuvants, which act as immune stimulators or antigen delivery systems, or both, encompass, for example, Alum, polysaccharides, liposomes, nanoparticles based on biodegradable polymers, lipopolysaccharides. Plasmid-encoded adjuvants encompass cytokines (such as IL-2, IL-12, IFN-γ, GM-CSF, IL-15), CpG motifs found on the plasmid backbone, chemokines, amongst others. Reference is made to Petrovsky et al. (Expert Rev Vaccines, 2012 February; 11(2): 189-209), for further details.

By contrast, “naked DNA immunization or vaccination” refers to DNA immunization or vaccination performed in the absence of adjuvant(s), which is an embodiment also encompassed within the present invention.

According to a particular embodiment, the invention makes use of a polypeptide, which:

a. has an amino-acid sequence having SEQ ID No1 or 2,
b. has an amino-acid sequence having at least 85%, preferably at least 90%, more preferably at least 95%, and most preferably at least 98% or 99% identity over their whole length with the amino-acid sequence having SEQ ID No1 or 2,
c. is a fragment of a. or b suitable for the elicitation of an immune response in a host, either a T cell and/or a B cell response.

The sequence disclosed in SEQ ID No2 encompasses a linker sequence of 12 amino-acids upstream of the polypeptidic sequence of the α3 domain of human HLA-G, serving the purpose of facilitating the dimerization of the corresponding polypeptide. This linker is however not considered by the inventors as bearing a particular function with respect to the goal achieved by the present invention, relative to the elicitation of antibodies.

Specific examples of polypeptide(s) are provided in the Results section herein, when immunization with a polypeptide sequence is performed.

The invention also relates to a composition comprising as an active ingredient an antibody or an antigen-binding fragment thereof or a chimeric molecule as disclosed herein, with a pharmaceutical vehicle such as an excipient, wherein said pharmaceutical composition optionally comprises a further, different, active ingredient.

By "active ingredient" it is meant an ingredient that is accountable for the produced biological effect. In a particular embodiment, such an active ingredient also possesses adjuvant property(ies).

According to the invention, a composition of the invention comprising as an active ingredient, an antibody or an antigen-binding fragment thereof or a chimeric molecule or a composition of the invention as disclosed herein can be:

a. for use as a medicament or as an active ingredient of a medicament, in particular for use as an immunotherapeutic vaccine, and/or;
b. for use in a host in need thereof, in particular a human patient, to interfer with and in particular to neutralize the immune down-regulation due to HLA-G proteins, and/or;
c. for use in a host in need thereof, in particular a human patient, for improving or treating conditions showing HLA-G+ lesions, i.e., conditions wherein HLA-G or of the pathways associated with HLA-G are dysfunctionally employed in cells of said host, in particular in order to favour the development of said condition or of a disease, and/or;
d. for use in a host in need thereof, in particular a human patient, for improving or treating a neoplasic condition or disease, in particular a cancer disease, in particular a condition or disease showing HLA-G+ lesions i.e., a condition or disease wherein HLA-G or of the pathways associated with HLA-G are dysfunctionally employed in cells of said host, in particular in order to favour the development of said condition or disease.

The effects of immune down-regulation due to HLA-G proteins are disclosed above, said immune down-regulation generally being the mechanism responsible of the "tumour escape" behaviour in hosts presenting such a condition. The concept of immune down-regulation due to HLA-G proteins is however intrinsic to the role of HLA-G proteins in a living body, and can therefore be found in any type of health status.

Therefore, the antibody or an antigen-binding fragment thereof or a chimeric molecule or a composition of the invention as disclosed herein can be used as a medicament, in particular can be used as a vaccine (elicitation of an immune response), in any host expressing HLA-G proteins.

By "host" it is meant an animal, especially a mammal, but also a human.

By "treating" it is meant curing, reversing, attenuating, alleviating, minimizing, suppressing or halting the effects of the condition or disease for which a treatment is sought.

By "medicament" or "vaccine", it is meant means appropriate for treating a host, as described above, in particular by eliciting an immune reaction in said host leading to the production of antibodies in said host.

According to a particular embodiment however, use of a composition of the invention comprising as an active ingredient, an antibody or an antigen-binding fragment thereof or a chimeric molecule or a composition of the invention as disclosed herein, in a host in need thereof, is made in combination with another living organism treatment method, such as, but non-exhaustively, chemotherapy treatment, radiotherapy treatment or the like.

Presence of "HLA-G+ lesions" depends on the condition or disease from which the host in need of a response against HLA-G is suffering. "HLA-G+ lesions" refer to the fact that HLA-G function or associated pathways can be found dysfunctionally employed within the context of a specific disease, notably favouring the development of said disease.

Therefore a composition of the invention comprising as an active ingredient, an antibody or an antigen-binding fragment thereof or a chimeric molecule as disclosed herein can be used for targeting and interfering at the cellular level with HLA-G function or associated pathways in a host in need thereof, when HLA-G proteins are found expressed by the host under a particular health status or condition.

Non-limitative examples of conditions that may present HLAG+ lesions are viral infections such as HIV infection, rabies virus infection or hepatitis B virus infection, autoimmune diseases implying immune cells expressing HLA-G with an $\alpha 3$ domain, notably chronic inflammations or malignant tumors.

Non-limitative examples of cancer diseases or neoplasic conditions, notably presenting HLA-G+ lesions are leukemia, basal cell carcinoma, bladder cancer, breast cancer, malignant mesothelomia, actinic keratosis, cutaneous melanoma, clear cell renal carcinoma, retinoblastoma, spinous cell carcinoma, in situ carcinoma, colorectal cancer, ovarian carcinoma, cutaneous T cell lymphoma, endometrial adenocarcinoma, classical Hodgkin lymphoma, lung carcinoma, cutaneous B cell lymphoma, gastric cancer, ampullary cancer, biliary cancer, pancreatic ductal adenocarcinoma, esophageal squamous cell carcinoma, hydatidiform moles.

"HLA-G+ lesions" may be present in less or more than 30% of the dysfunctional cells present in the host. According to a particular embodiment however, a minimum of 10% of cells presenting HLA-G+ lesions is sufficient to qualify the disease as presenting "HLA-G+ lesions".

The invention also relates to a method of production of an antibody or a antigen-binding fragment thereof according to the present invention, which comprises:

a. Administering to a non-human animal, a nucleic acid encoding a polypeptide having the amino-acid sequence SEQ ID No1 or 2, or an amino-acid sequence having at least 85%, preferably at least 90%, more preferably at least 95%, and most preferably at least 98% or 99% identity over their whole length with the amino-acid sequence having SEQ ID No1 or 2 or administering nucleic acid(s) of the invention as disclosed herein, in particular a nucleic acid molecule comprising or consisting of the nucleotide sequence of SEQ ID No9 or derived from this sequence, or immunogenic fragments thereof, or a vector comprising or consisting of a nucleic acid molecule comprising or consisting of the nucleotide sequence of SEQ ID No9 or derived from this sequence, or immunogenic fragments thereof, in particular a vector of the invention as disclosed or discussed herein, and,
b. Recovering from sera or plasma samples obtained from the animals the elicited antibodies and checking their specificity for the $\alpha_3$ domain of HLA-G protein, and;
c. Optionally, cloning the recovered antibodies, and
d. Optionally, preparing antigen-binding fragments from the recovered antibodies.

Administration, recovery of generated antibodies or antigen-binding fragments and subsequent cloning can be achieved through conventional methods in the art. Characterization methods prior to cloning using par example advanced sequencing methods are also well known in the art.

In a particular embodiment of the invention step a. is not claimed and step b. is performed on a sample previously obtained from an animal having received the component as defined in step a.

The preparation of antigen-binding fragments from the recovered antibodies can also be achieved through conventional methods in the art, in particular through high-throughput synthesis technologies.

Host animals for antibodies or antigen-binding fragments production can be mammals to the exclusion of the human, especially rodents, in particular mice.

According to a particular embodiment, the method of production disclosed herein also involves a step of sacrificing the host animals used for the production of the antibodies of the invention.

According to a particular embodiment, the method of production of an antibody or an antigen-binding fragment thereof according to the present invention encompasses the concomitant administration, in step a., of an adjuvant, the latter being defined as any ingredient, in particular compound, that acts to assist, accelerate, prolong or enhance antigen-specific immune responses when used in combination with administrated antigen(s) or immunogenic antigen fragment(s). Adjuvants are well known in the art of immunization (or vaccination) and immune-therapy.

As stated before, with respect to embodiments involving DNA immunization, adjuvants may be integrated in the vectors (or plasmids) used for DNA immunization.

By "immunogenic fragment", it is meant a fragment retaining the capacity of inducing an immune response in the host animal administered with said fragment, in order to enable the production of antibodies of the invention as disclosed herein.

According to a particular embodiment, administration according to step a. of the above-disclosed method is performed using a prime-boost immunization protocol implying a first administration (prime immunization or prime administration) of active immunogenic agents, and then at least one further administration (boost immunization or boost administration) that is separated in time from the first administration within the course of the immunization protocol. Boost immunizations encompass one, two, three or more administrations.

In a particular embodiment, the used prime-boost immunization protocol is either an homologous or an heterologous immunization protocol, meaning that the administered active, immunogenic, ingredients (e.g. antibodies or fragments) are respectively the same in the prime and boost administrations, or different.

In a particular embodiment, administration of active, immunogenic, ingredients in step a. of the above-mentioned method, including when a prime administration is performed and/or when a boost immunization is performed, is made concomitantly with an adjuvant, for example a Freund's adjuvant. Adjuvants are substances well known in the art.

In a specific embodiment, adjuvant administration is performed at both prime and boost immunizations, in particular when polypeptides or immunogenic fragments thereof are used for immunization.

Details of an immunization protocol that may be used as is or serve as a basis to design an immunization protocol aimed at producing antibodies or antigen-binding fragments thereof using DNA immunization are given in the Example section below. Reference can also be made to Chapter 40 of *Electroporation Protocols: Preclinical and Clinical Gene Medicine from Methods in Molecular Biology*, vol. 423, pages 509-520, by C. K. Yan et al. Examples of period of time left between a prime immunization and boost immunization, or subsequent boost administrations, are given in the Material and Methods section herein, as well as in the Chapter cited above or in the literature.

The present invention relies on experiments carried out using protein immunization and DNA immunization, as illustrated in the Results section herein. Illustrative protein immunization was carried out using a polypeptide having the polypeptide sequence SEQ ID No2. Illustrative DNA immunizations were carried out using a plasmid comprising the nucleotide sequence disclosed under SEQ ID No6. As illustrated below, SEQ ID No2 encompasses two amino-acid residues after the linker sequence, namely residues R and A, belonging to the end of the α2 domain of HLA-G, according to the definitions provided herein, as well as two amino-acid residues after the α3-domain portion, which belong to a transmembrane anchor domain. In the literature, for example in McCluskey et al. (PNAS 2005, vol. 102, no. 9, 3360-3365 *Crystal structure of HLA-G: A nonclassical MHC class I molecule expressed at the fetal-maternal interface*), the two amino-acid residues R and A discussed above may however be considered as belonging to the α3 domain of HLA-G. The definition of the α3 domain of HLA-G may therefore slightly depend upon the annotations considered in the literature, but not by more than a few amino-acid residues. In addition, it was ascertained by the inventors that the antibodies were raised against the α3 portion of the polypeptide as defined herein. SEQ ID No6, as detailed below, also encompasses, in addition to a portion encoding for the α3 domain of HLA-G as defined herein, several nucleotide bases belonging to either the signal peptide found in the exon 1 of HLA-G, or the very end of the α2 domain of HLA-G, or a transmembrane anchor. It was however ascertained by the inventors that, within the conditions of the experimentations carried out, antibodies of the invention were specifically raised against the α3 domain of HLA-G as defined herein.

The invention also relates to an antibody or an antigen-binding fragment thereof obtainable or obtained by the method of production as disclosed above.

The invention also relates to a polyclonal serum obtained from the implementation of step a. of the method of the invention as disclosed above.

According to particular embodiments, such antibody or an antigen-binding fragment thereof obtainable or obtained by the method of production as disclosed above or polyclonal serum obtained from the implementation of step a. of the method of the invention as disclosed above are obtained through DNA immunization of a host, in particular a mammal such as a rodent, as described herein.

The invention also relates to an immunogenic composition comprising a nucleic acid molecule, a vector or cell according to the invention or a nucleic acid molecule comprising or consisting of the nucleotide sequence of SEQ ID No9 or derived from this sequence, or a polypeptide that either (i) has an amino-acid sequence having SEQ ID No1 or 2, or (ii) has an amino-acid sequence having at least 85%, preferably at least 90%, more preferably at least 95%, and most preferably at least 98% or 99% identity over their whole length with the amino-acid sequence having SEQ ID No1 or 2, or (iii) a fragment of (i) or (ii), and a pharmaceutically acceptable vehicle, wherein said immunogenic composition optionally comprises a further, different, active ingredient and/or an adjuvant, as already defined herein.

The invention also relates to nucleic acid molecules, vectors, cells or compositions according to invention, including a nucleic acid molecule comprising or consisting of the nucleotide sequence of SEQ ID No9, or to a polypeptide that either (i) has an amino-acid sequence having SEQ ID No1 or 2, or (ii) has an amino-acid sequence having at least 85%, preferably at least 90%, more preferably at least 95%, and most preferably at least 98% or 99% identity over their whole length with the amino-acid sequence having SEQ ID No1 or 2, or (iii) a fragment of (i) or (ii):

for use as a medicament, in particular for use as a therapeutic vaccine, in a mammal, in particular a human, especially as a DNA vaccine, in particular for use as a naked DNA vaccine, and/or;

for use to elicit, in particular in a host such as a mammal, in particular a human or a rodent, an immune response against the α3 domain of HLA-G protein and produce antibodies or antigen-binding fragments thereof which specifically binds the α3 domain of HLA-G protein, as disclosed within the present invention.

These nucleic acid molecules, vectors, cells or compositions according to invention referred to above may be used to elicit an immune response in a mammal host, in particular a human, through a prime-boost immunization protocol, especially a prime-boost immunization protocol that is adjuvanted either at the prime or at the boost administrations, or both. These nucleic acid molecules, vectors, cells or compositions according to invention referred to above may also be used to elicit an immune response in a mammal host, in particular a human, through an heterologous immunization protocol.

Also, the nucleic acid molecules, vectors, cells or compositions according to invention, as disclosed herein, can be used as a medicament, in particular can be used as a vaccine (elicitation of an immune response), in any host expressing HLA-G proteins.

It can be seen from the preceding that the present invention and means disclosed herein are suitable in a context of immunotherapy(ies), in particular neoplasic diseases or cancer immunotherapy(ies). Immunotherapy is defined as the treatment of a disease by inducing, or enhancing an immune response. The present invention is indeed particularly relevant to assist the elimination of the tumour-escape mechanism involved in some neoplasic diseases or cancers.

The invention also relates to a method for treating a condition or disease wherein the pathways associated with HLA-G are involved, according to all the embodiments described herein, comprising a step of administering antibodies or antigen-binding fragments thereof described herein, or polyclonal serum comprising the same, chimeric molecules as described herein, nucleic acid molecules described herein, vectors or cells or compositions, including immunogenic compositions of the invention, in a host in need thereof, by reference to the statements provided herein, for prophylactic or therapeutic or vaccination purposes, as developed herein.

The invention also relates to an in vitro method for detecting HLA-G protein in a sample and/or monitoring or diagnosing a health status or pathologic condition through the analysis of a sample previously obtained from a patient susceptible of presenting a specific health status or having a pathologic condition, in particular a neoplasic condition, said method comprising:

a. Contacting, in conditions enabling the formation of immune complexes, the sample with antibodies or antigen-binding fragment thereof or a chimeric molecule as disclosed herein, and
b. Detecting in vitro the resulting immune complexes formed between said antibodies or antigen-binding fragments thereof and HLA-G protein, as disclosed herein.

According to a particular embodiment, the present invention enables the in vitro detection of HLA-G protein in a sample, for example a sample previously obtained from a patient susceptible of being pregnant, or a sample obtained from a patient having undergone organ or tissue or cell transplantation(s). As a result, the monitoring of a health status can be performed, i.e. a physiological status that does not necessarily involve the presence of a pathologic condition. Subsequent diagnosis of the presence or absence of a pathologic condition can therefore also be performed.

When the sample has been previously obtained from a patient susceptible of presenting a pathologic condition, subsequent monitoring or diagnosis of such a pathologic condition may also be performed. In a particular embodiment, pathologic conditions referred to are those disclosed above.

According to a particular embodiment, the antibodies or antigen-binding fragments thereof of the invention, which recognize β2M-free HLA-G protein isoform(s), are of particular interest for detection or diagnosis purposes.

The invention also relates to a kit for an in vitro assay or diagnosis method as disclosed above, said kit comprising:

a. At least one compound selected from the group consisting in: an antibody or antigen-binding fragment thereof or a chimeric molecule as disclosed herein,
b. Reagent(s) appropriate for the formation of immune complex(es) between at least one compound listed in a. and the sample to assay;
c. Optionally, reagent(s) appropriate for detecting the formation of the immune complexe(s) of step b.

Other examples and features of the invention will be apparent when reading the results obtained by the inventors and the figures, which illustrate the experiments conducted by the inventors, in complement to the features and definitions given in the present description.

FIGURES LEGENDS

FIG. 1: HLA-G protein isoforms

FIG. 2: Overall structure of the LILRB2 complex of HLA-G

Figure 3:
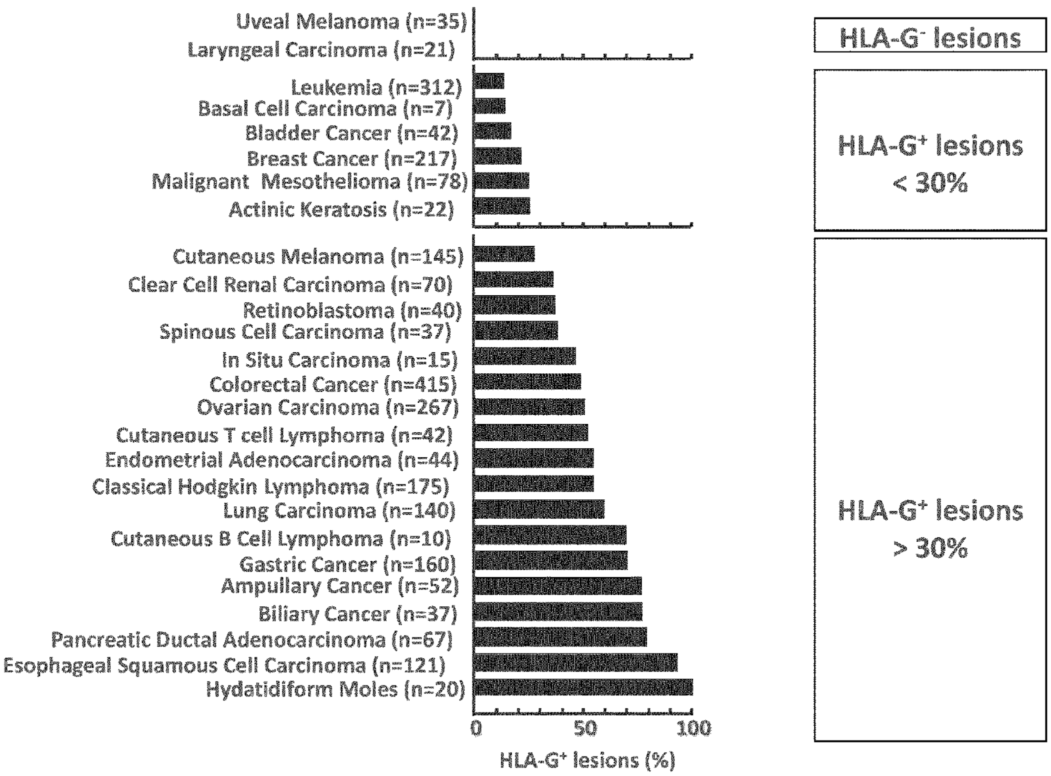

FIG. 3: HLA-G expression in tumor lesions

Figure 4:
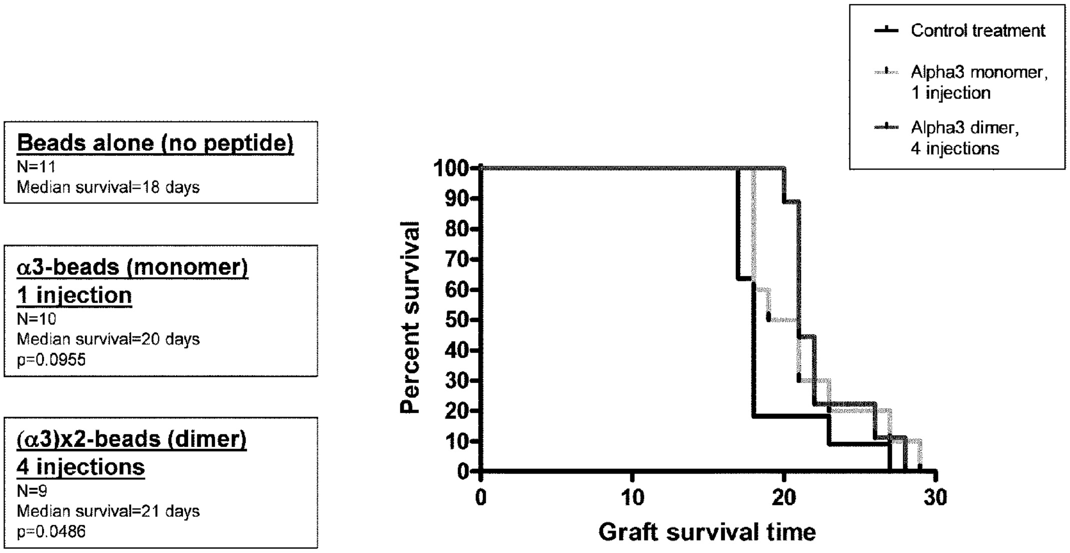
Figure 5:
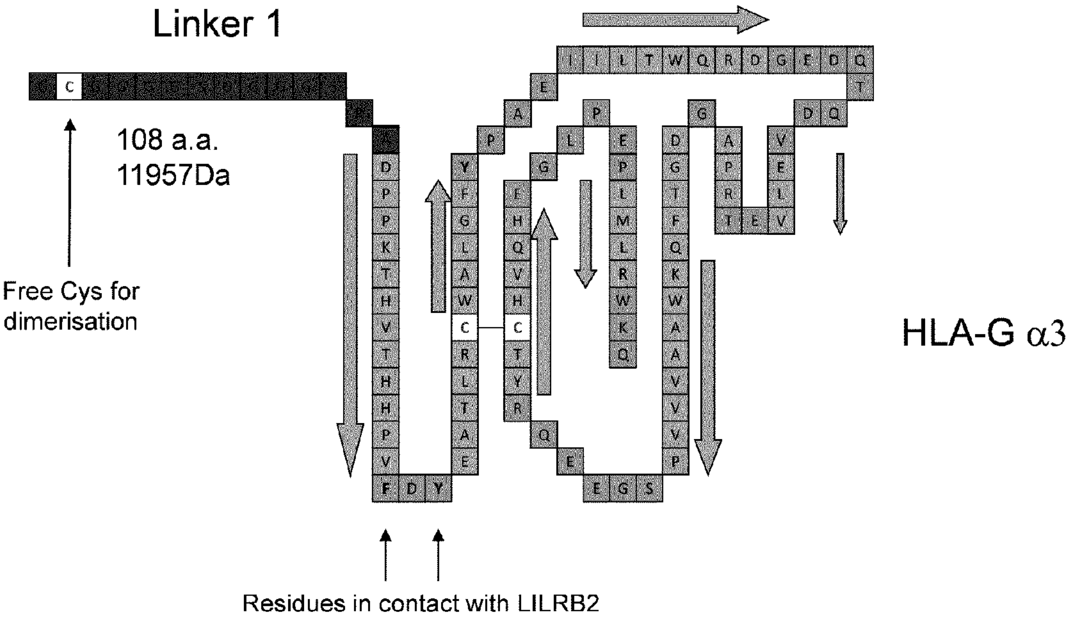

FIG. 4: In vivo experiments: no tolerogenic effect of $\alpha_3$ and $(\alpha_3)\times2$ molecules after skin allograft in mice FIG. 5: Constructs details of HLA-G $\alpha_3$ domain proteins (SEQ ID No12)

Figure 6:
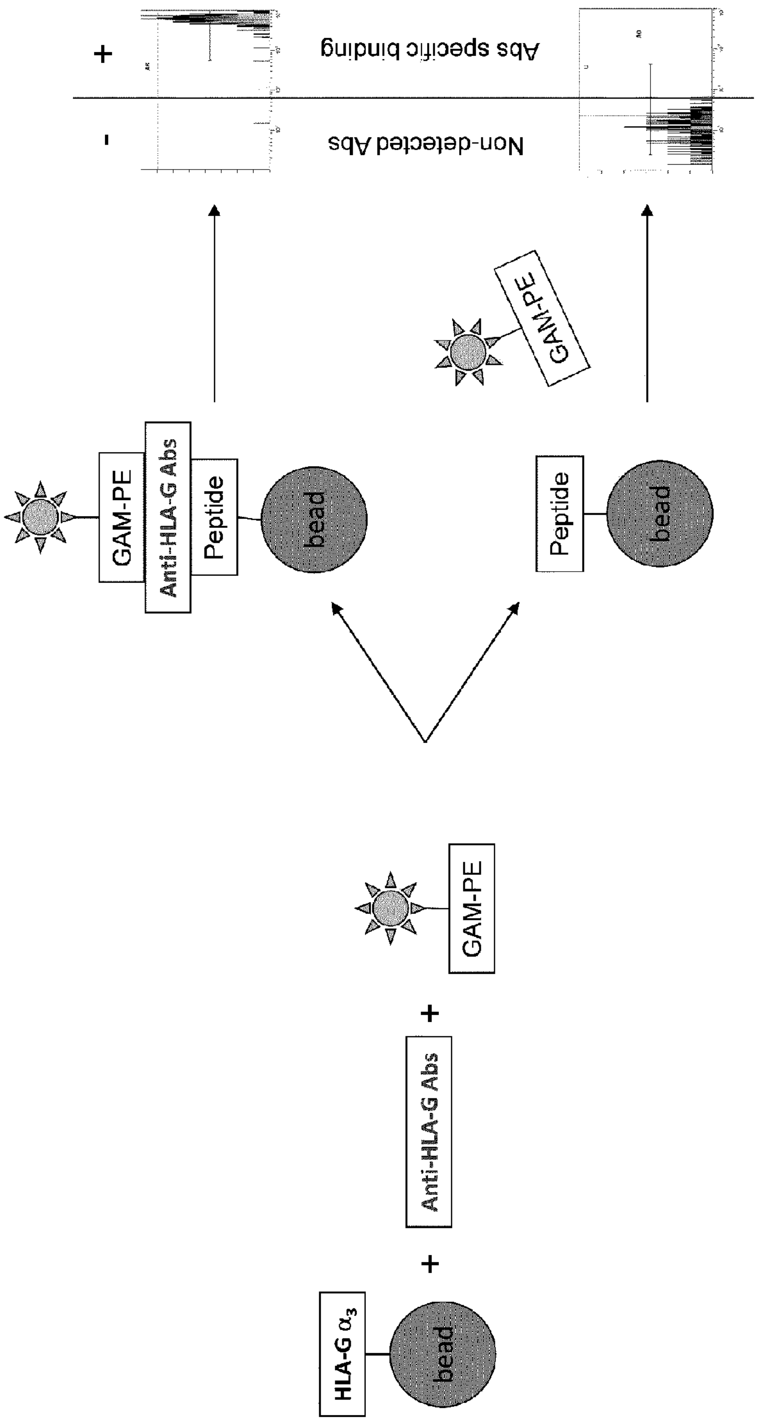

FIG. 6: Luminex method principle to detect specific binding of HLA-G $\alpha_3$ domain protein by anti-HLA-G antibodies FIG. 7: anti-HLA-G $\alpha_3$ domain protein antibodies detected in plasmas of protein-immunized C57Bl/6J HLA-B*0702 transgenic mice after 4th boost by (A) ELISA, (B) Luminex beads and (C) slot-blot assay.

Figure 8A:
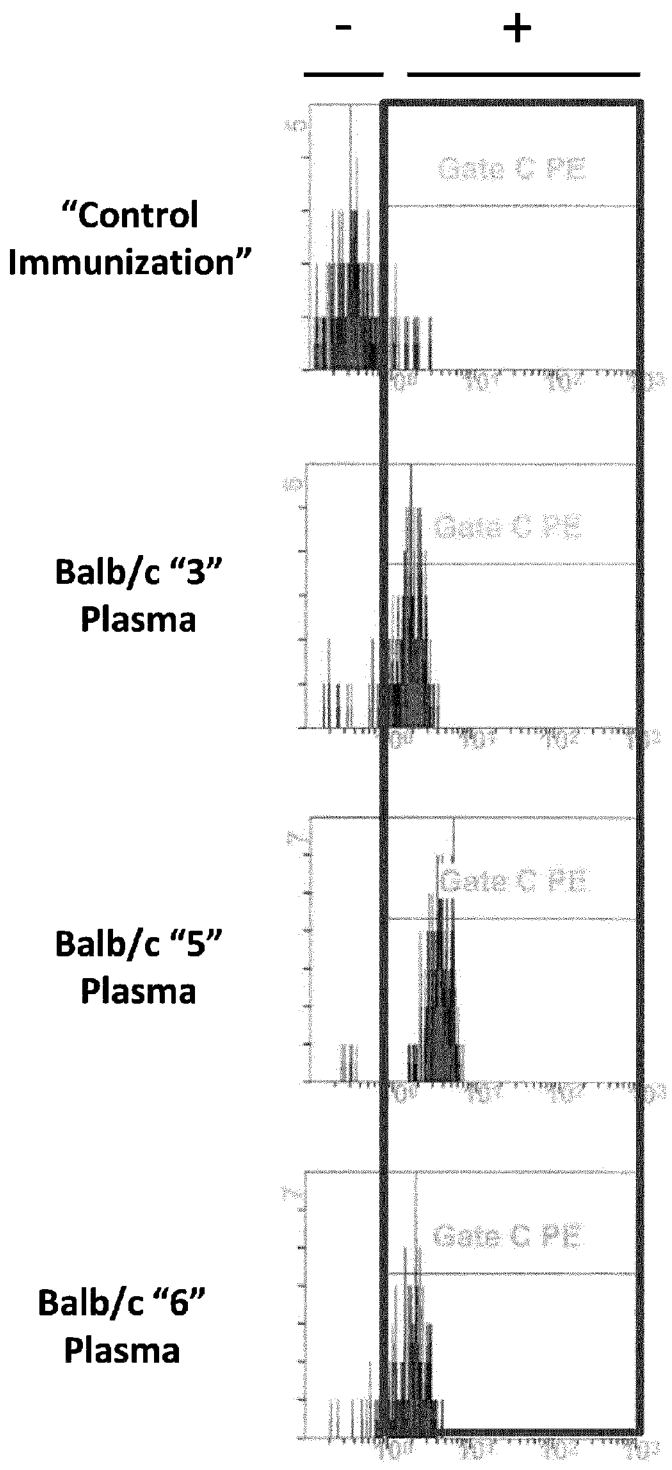
Figure 8B:
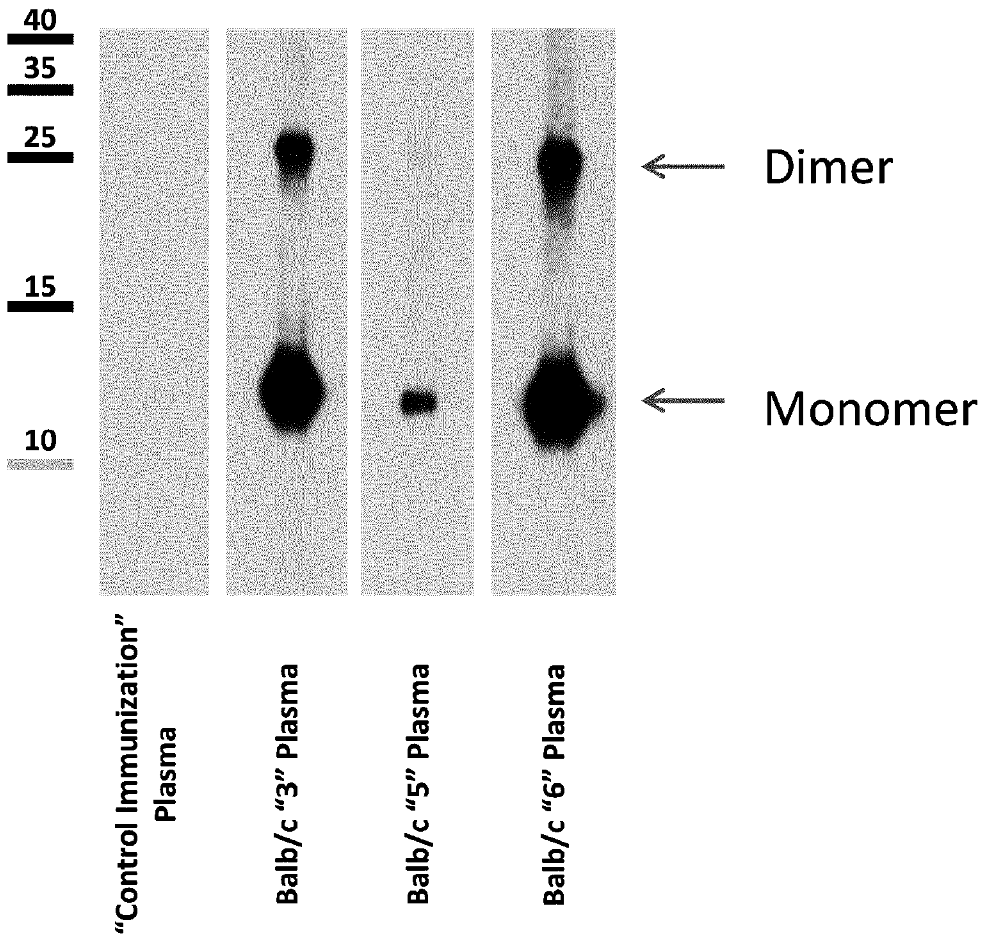
Figure 9A:
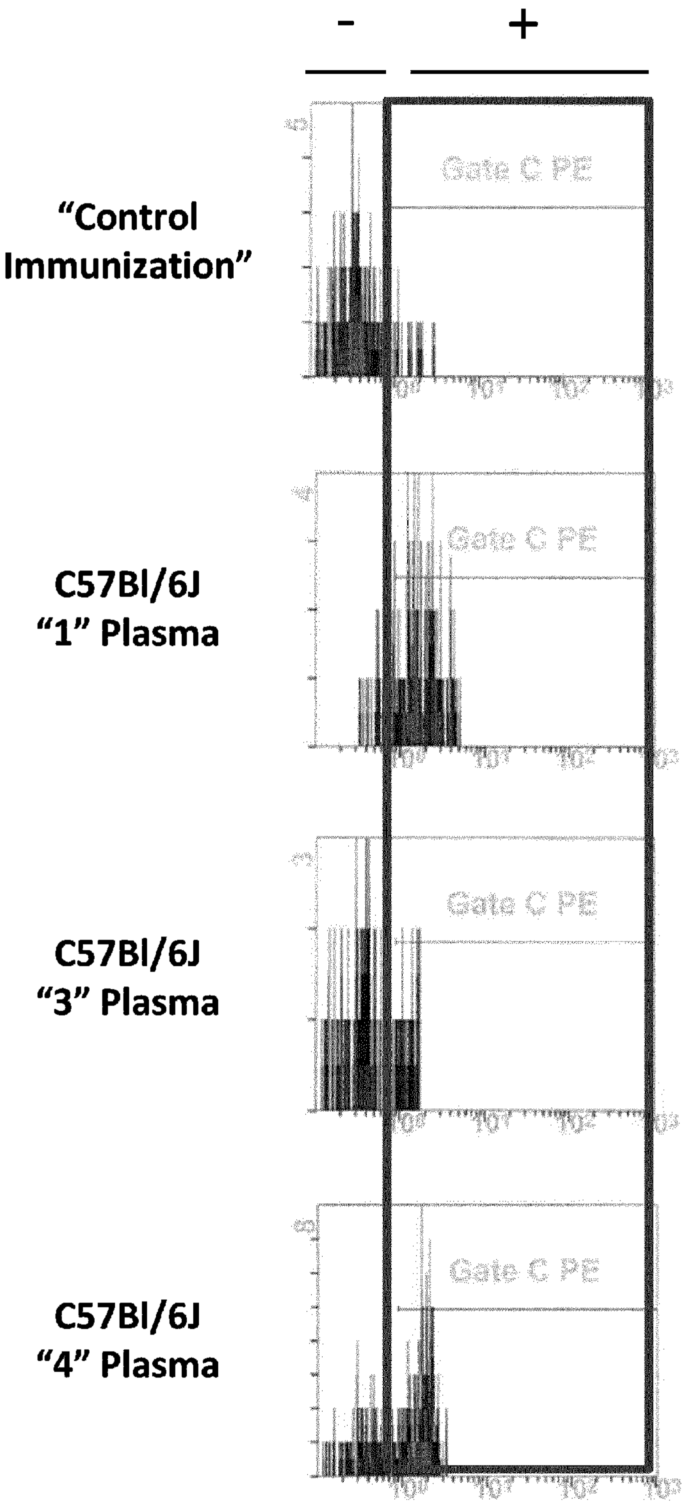
Figure 9B:
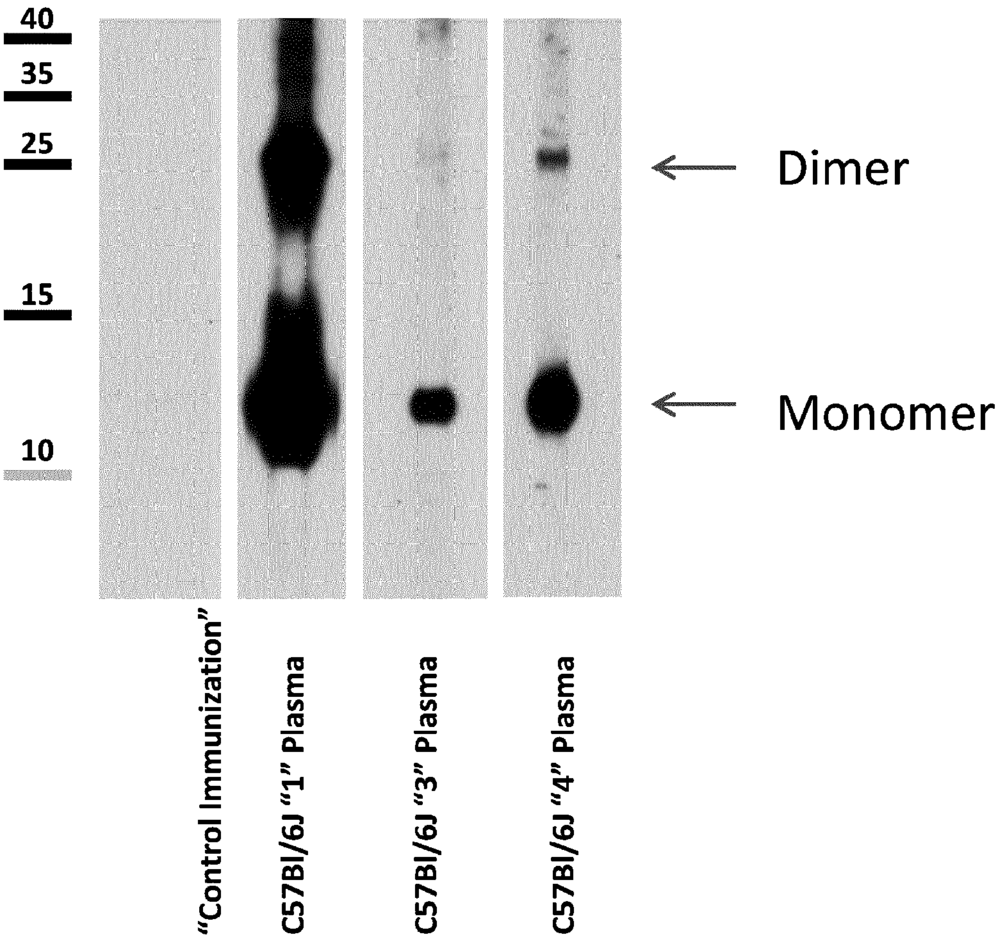
Figure 10:
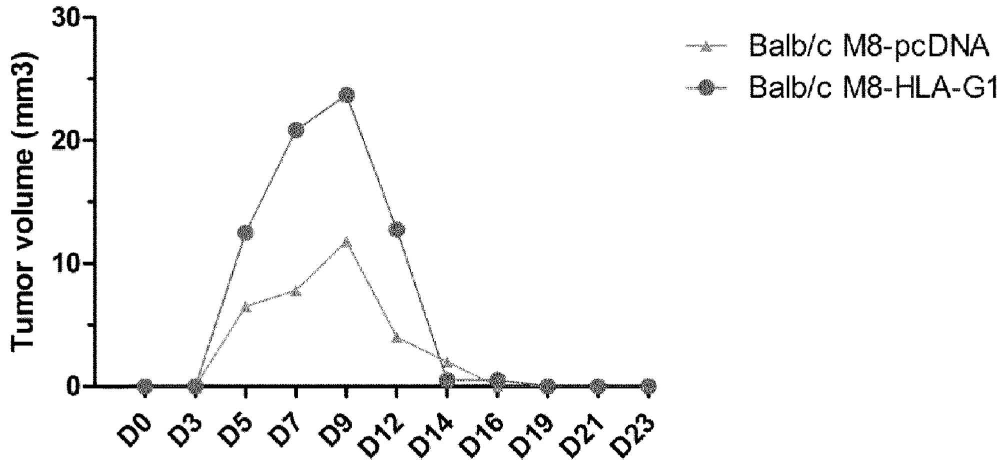

FIG. 8: anti-HLA-G $\alpha_3$ domain protein antibodies in plasmas of DNA-immunized Balb/c mice after 2nd boost (4 weeks) detected (A) by Luminex beads and (B) by Slot-blot assay FIG. 9: anti-HLA-G $\alpha_3$ domain protein antibodies in plasmas of DNA-immunized C57Bl/6J mice after 2nd boost (3 weeks) detected (A) by Luminex beads and (B) by slot-blot assay FIG. 10: No DNA HLA-G-α3 vaccination: $2\cdot10^6$ M8-pcDNA or M8-HLA-G1 were implanted subcutaneously on Balb/c mice (M8-pcDNA: Human Melanoma transfected with pcDNA 3.1 control plasmid; M8-HLA-G1: Human Melanoma transfected with pcDNA 3.1 plasmide containing HLA-G1 sequence). Tumor volume according to the Human Melanoma concentration is plotted. No antibodies against HLA-G-α3 domain were detected in non-immunized mice monitored before tumor challenge.

Figure 11:
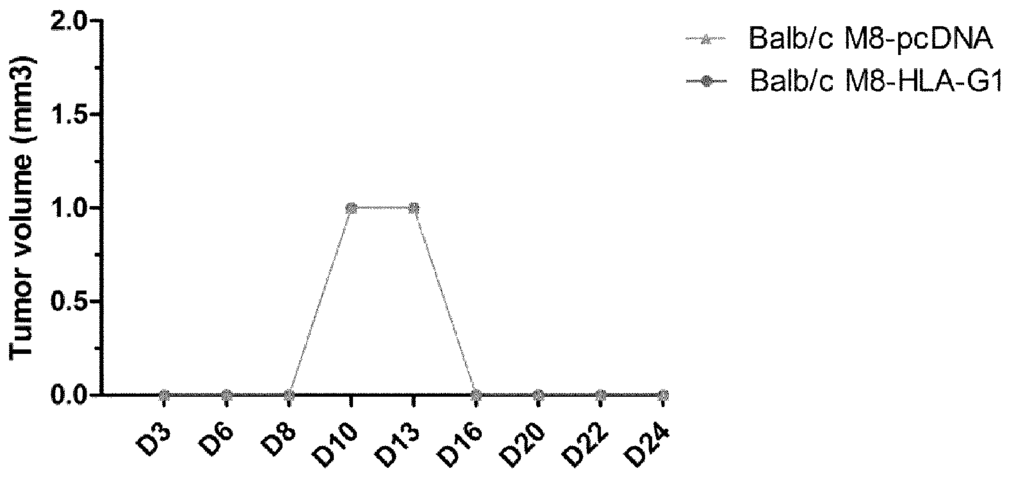

FIG. 11: DNA HLA-G-α3 vaccination: $2 \cdot 10^6$ M8-pcDNA or M8-HLA-G1 were implanted subcutaneously on Balb/c mice (M8-pcDNA: Human Melanoma transfected with pcDNA 3.1 control plasmid; M8-HLA-G1: Human Melanoma transfected with pcDNA 3.1 plasmide containing HLA-G1 sequence). As described in the Materials and Methods section, Balb/c mice were immunized 4 times with HLA-G-α3 DNA. Induction of antibodies against HLA-G-α3 domain was monitored before tumor challenge: all Balb/c mice generated anti-HLA-G-α3 antibodies after DNA immunization. Tumor volume according to the Human Melanoma concentration is plotted.

MATERIALS AND METHODS

```
SEQ ID No 1: HLA-Galpha3 or HLA-Gα3 protein
sequence
DPPKTHVTHHPVFDYEATLRCWALGFYPAEIILTWQRDGEDQTQDVELVE
TRPAGDGTFQKWAAVVVPSGEEQRYTCHVQHEGLPEPLMLRW
```

SEQ ID No1 is based on the disclosure found in McCluskey et al. (PNAS 2005, vol. 102, no. 9, 3360-3365 *Crystal structure of HLA-G: A nonclassical MHC class I molecule expressed at the fetal-maternal interface*), and/or derived from the full HLA-G human protein as found in the literature or under accession number NM_002127.5, referred to as SEQ ID No4 herein.

```
SEQ ID No 4:
MVVMAPRTLFLLLSGALTLTETWAGSHSMRYFSAAVSRPGRGEPRFIAMG

YVDDTQFVRFDSDSACPRMEPRAPWVEQEGPEYWEEETRNTKAHAQTDRM

NLTLRGYYNQSEASSHTLQWMIGCDLGSDGRLLRGYEQYAYDGKDYLALN

EDLRSWTAADTAAQISKRKCEAANVAEQRRAYLEGTCVEWLHRYLENGKE

MLQRADPPKTHVTHHPVFDYEATLRCWALGFYPAEIILTWQRDGEDQTQD

VELVETRPAGDGTFQKWAAVVVPSGEEQRYTCHVQHEGLPEPLMLRWKQS

SLPTIPIMGIVAGLVVLAAVVTGAAVAAVLWRKKSSD
```

The “natural”, i.e. not engineered or found naturally in living organisms, nucleic acid sequence encoding a HLA-Gα3 domain polypeptide sequence can be found in the sequence disclosed under accession number NM_002127.5, between positions 797 and 1072 (276 pb), and is referred to as SEQ ID No 9 herein.

```
                                     SEQ ID No 9
gaccccccaagacacacgtgacccaccaccctgtctttgactatgaggc

caccctgaggtgctgggccctgggcttctaccctgcggagatcatactga

cctggcagcgggatggggaggaccagacccaggacgtggagctcgtggag

accaggcctgcaggggatggaaccttccagaagtgggcagctgtggtggt

gccttctggagaggagcagagatacacgtgccatgtgcagcatgaggggc

tgccggagcccctcatgctgagatgg
```

An example of an optimized nucleic acid sequence, which is considered optimized by comparison to SEQ ID No 9 defined herein, and encoding for an HLA-Gα3 domain polypeptide sequence, is disclosed and referred to as SEQ ID No 10 herein.

```
gaccccccaaaacccatgtgacccaccacccagtctttgactatgaa

gctacactgagatgttgggccctgggcttctaccccgcagagatcatc

ctgacctggcagcgcgacggagaagatcagacacaggacgtcgagctc

gtggaaacccggcctgctggtgatggcacatttcagaagtgggccgcc

gtggtggttccatccggtgaggaacagcgctacacttgccatgtgcag

cacgagggcttgcctgagcctcttatgcttcggtgg
```

The full human HLA-G nucleic sequence disclosed under accession number NM_002127.5 is disclosed herein as SEQ ID No 5:

```
agtgtggtac tttgtcttga ggagatgtcc tggactcaca

cggaaactta gggctacgga atgaagttct cactcccatt

aggtgacagg tttttagaga agccaatcag cgtcgccgcg

gtcctggttc taaagtcctc gctcacccac ccggactcat

tctccccaga cgccaaggat ggtggtcatg gcgccccgaa

ccctcttcct gctgctctcg gggggccctga ccctgaccga

gacctgggcg ggctcccact ccatgaggta tttcagcgcc

gccgtgtccc ggcccggccg cggggagccc cgcttcatcg

ccatgggcta cgtggacgac acgcagttcg tgcggttcga

cagcgactcg gcgtgtccga ggatggagcc gcgggcgccg

tgggtggagc aggaggggcc ggagtattgg gaagaggaga

cacggaacac caaggcccac gcacagactg acagaatgaa

cctgcagacc ctgcgcggct actacaacca gagcgaggcc

agttctcaca ccctccagtg gatgattggc tgcgacctgg

ggtccgacgg acgcctcctc cgcgggtatg aacagtatgc

ctacgatggc aaggattacc tcgccctgaa cgaggacctg

cgctcctgga ccgcagcgga cactgcggct cagatctcca

agcgcaagtg tgaggcggcc aatgtggctg aacaaaggag

agcctacctg gagggcacgt gcgtggagtg gctccacaga

tacctggaga acgggaagga gatgctgcag cgcgcggacc

cccccaagac acacgtgacc caccaccctg tctttgacta

tgaggccacc ctgaggtgct gggccctggg cttctaccct

gcggagatca tactgacctg gcagcgggat ggggaggacc

agacccagga cgtggagctc gtggagacca ggcctgcagg

ggatggaacc ttccagaagt gggcagctgt ggtggtgcct

tctggagagg agcagagata cacgtgccat gtgcagcatg
```

-continued

```
aggggctgcc ggagcccctc atgctgagat ggaagcagtc

ttccctgccc accatcccca tcatgggtat cgttgctggc

ctggttgtcc ttgcagctgt agtcactgga gctgcggtcg

ctgctgtgct gtggagaaag aagagctcag attgaaaagg

agggagctac tctcaggctg caatgtgaaa cagctgccct

gtgtgggact gagtggcaag tccctttgtg acttcaagaa

ccctgactcc tctttgtgca gagaccagcc cacccctgtg

cccaccatga ccctcttcct catgctgaac tgcattcctt

ccccaatcac ctttcctgtt ccagaaaagg ggctgggatg

tctccgtctc tgtctcaaat ttgtggtcca ctgagctata

acttacttct gtattaaaat tagaatctga gtataaattt

actttttcaa attatttcca agagagattg atgggttaat

taaaggagaa gattcctgaa atttgagaga caaaataaat

ggaagacatg agaacttt
```

Immunizing Agents

Protein Immunization

The HLA-G $\alpha_3$ domain used for protein immunization was produced by chemical synthesis (Patent: WO 2010/150233). This protein is made up of 108 amino acids, of molecular weight 11957 Da, and is composed by the following protein sequence (SEQ ID No2), for which the first 12 amino acids contain a linker sequence (SEQ ID No 3):

GCGGGGSGGGGSRADPPKTHVTHHPVFDYEATLRCWALGFYPAEIILTWQ
RDGEDQTQDVELVETRPAGDGTFQKWAAVVVPSGEEQRYTCHVQHEGLPE
PLMLRWKQ

SEQ ID No 3:
GCGGGGSGGGGS

DNA Immunization

For DNA immunization, the sequence of the $\alpha_3$ domain was fused to the simian virus 5 V5 protein tag sequence, the ensemble was cloned into the pcDNA 3.1(+) plasmid vector (Invitrogen) by the HindIII and XhoI restriction sites (underlined). The nucleotide sequence used is (SEQ ID No 6):

5'AAGCTTGCCGCC*Atggtcgttatggcacccaggaccttgttcctcct*
*gctctctggag*cactgacccttactgagacatgggcc*agtagagcc*ga
ccccccaaaacccatgtgacccaccacccagtctttgactatgaagcta
cactgagatgttgggccctgggcttctaccccgcagagatcatcctgacc
tggcagcgcgacggagaagatcagacacaggacgtcgagctcgtggaaac
ccggcctgctggtgatggcacatttcagaagtgggccgccgtggtggttc
catccggtgaggaacagcgctacacttgccatgtgcagcacgagggcttg
cctgagcctcttatgcttcggtggaagcagtcatccctgccaactattcc
catcatgggcattgtggccggactggtggttctggcagctgtggtgactg
**gcgctgccgtcgccgctgtcctctggaggaaaaagagcagc*gat***ggca*
*agccaattcctaatccattgctgggcctggactcaact*tgaTGATAACTC
GAG3'

Legend for SEQ ID No 6:

(SEQ ID No7) GCCGCCAtg at 5' extremity: 5' Kozak sequence

Signal Peptide as Found in Exon 1 of HLA-G

Nucleotides encoding added amino-acids

Nucleotides found at the end of the α2 (alpha2) portion of HLA-G α3 (alpha3) domain (corresponding to SEQ ID No10)

Transmembrane-Anchor Protein Encoding Portion

V5-tag sequence (SEQ ID No8) tgaTGATAA at 3' extremity: 3' Stop codon

The sequence cloned into the pcDNA 3.1(+) plasmid vector between GCCGCCA (SEQ ID No7) and tgaTGATAA (SEQ ID No8) has therefore a length of 534 pb.

The HindIII and Xho sites are underlined while the V5 sequence corresponding to the simian virus 5 V5 tag is shown in italics, according to the legend provided above. The gene was synthesized by GeneGust after codon optimization with respect to the natural nucleic acid sequence to eliminate low abundance codons.

For illustration purposes, the protein sequence (SEQ ID No 11) corresponding to, i.e. encoded by, the nucleic acid sequence elaborated for DNA immunization is given below. Domains α1 (alpha1) and α2 (alpha2) were deleted leaving a signal peptide (also found in the exon1 portion of HLA-G), two amino-acids of the end of the α2 (alpha2) domain, the α3 (alpha3) domain and a transmembrane anchor sequence, as annotated below.

SEQ ID No 11
*MVVMAPRTLFLLLSGALTLTETWA*SRADPPKTHVTHHPVFDYEATLRCWA
LGFYPAEIILTWQRDGEDQTQDVELVETRPAGDGTFQKWAAVVVPSGEEQ
RYTCHVQHEGLPEPLMLRWKQSSLPTIPIMGIVAGLVVLAAVVTGAAVAA
VLWRKKSSD*GKPIPNPLLGLDST*

Legend for SEQ ID No11:

Signal Peptide as Found in Exon 1 of HLA-G

Added Amino-Acids

Amino-acids found at the end of the α2 (alpha2) portion of HLA-G α3 (alpha3) domain (corresponding to SEQ ID No1)

Transmembrane-Anchor Protein Encoding Portion

V5-tag sequence

The nucleic acid sequence disclosed under SEQ ID No6 is not the same as that in the database under NM_002127.5 (SEQ ID No5), especially between positions 797 and 1072 corresponding to a portion encoding a polypeptide encompassing the α3 domain of HLA-G protein, as well as in the portion encoding a peptide signal and a transmembrane anchor. Most of the codons have been changed with 12 codons not being used at all. This is called codon optimization, according to conventional methods. The present rule set eliminates rare tRNAs and codons that are used infrequently in the human genome, infrequently being defined as <10%. Consequently the following codons were eliminated: Leu TTA, Leu CTA, Ile ATA, Val GTA, Ser TCG, Pro CCG, Thr ACG, Ala GCG, Gln CAA, Arg CGT, Arg CGA and Gly GGG.

The correspondence between the "natural" nucleic sequence of HLA-G and the optimized nucleic acid sequence used for experiments herein is provided below: optimized SEQ ID No6 is depicted with interlineated nucleotide bases, which are the nucleotide bases found in the "natural" nucleic sequence of HLA-G.

AAGCTT GCCGCC

*Atggtcgttatggcacccaggaccttgttcctcctgctctctggagcactgacccttactga* g  c     g   c  a  c c     g        g  g  c       g  c

*gacatgggcc*agtagagccgacccccccaaaacccatgtgacccaccacccagtctttgact c     g  cgcgcg           g  a  c             t atgaagctacactgagatgttgggccctgggcttctaccccgcagagatcatcctgacctgg g  c  c    g  c                    t  g       a cagcgcgacggagaagatcagacacaggacgtcgagctcgtggaaacccggcctgctggtga g  t  g  g  c     c       g           g  a       a  g tggcacatttcagaagtgggccgccgtggtggttccatccggtgaggaacagcgctacactt a  c  c          a  t        g  t  t  a     g  aga     g gccatgtgcagcacgagggcttgcctgagcctcttatgcttcggtggaagcagtcatccctg t     gc    g     c  c    ga a           t ccaactattcccatcatgggcattgtggccggactggtggttctggcagctgtggtgactgg c  c  c          t  c  t  t  c     t  c  t        a  c cgctgccgtcgccgctgtcctctggaggaaaaagagcagcgat*ggcaagccaattcctaatc* a      g     t   g  g     a  g      tca

*cattgctgggcctggactcaact*tgaTGATAA CTCGAG

Legend:

HindIII and XhoI Restriction Sites (SEQ ID No7) GCCGCCAtg at 5' extremity: 5' Kozak sequence Signal Peptide as Found in Exon 1 of HLA-G Added Amino-Acids Nucleotides found at the end of the α2 (alpha2) portion of HLA-G α3 (alpha3) domain (corresponding to SEQ ID No10)

Transmembrane-Anchor Protein Encoding Portion

V5-tag sequence (SEQ ID No8) tgaTGATAA at 3' extremity: 3' Stop codon

With respect to the nucleotide sequence encoding for the α3 (alpha3) domain, 46 nucleotides were modified over the 276 nucleotides of said domain.

As previously stated, the coding sequence was bounded at 5' extremity by a good Kozak initiation sequence (GCCGCCATG (SEQ ID No7), initiator codon in bold face) and a pair of stop codons at 3' extremity (TGATAA (SEQ ID No8) in bold face), the ensemble being flanked by 5' HindIII and 3' XhoI restriction sites (underlined). The DNA insert was synthesized by GeneGust and cloned into the expression vector pcDNA3.1+ by way of the HindIII and XhoI sites.

The resulting sequence is disclosed under SEQ ID No6, which encodes a HLAG signal peptide, the α3 domain of human HLA-G, a HLA-G transmembrane spanning sequence fused to the simian virus 5 V5 protein tag sequence, with a 5' Kozak initiation sequence and a 3' pair of stop condons, and HindIII and XhoI restriction sites.

Plasmid production, transfection and electroporation were performed using standard techniques.

Mice

C57Bl/6J HLA-B*0702 transgenic mice bred in Institut Pasteur's animal facility were used for protein immunization (8 weeks of age). Balb/c and C57Bl/6J mice (8 weeks of age) were obtained from Janvier Laboratories and used for DNA immunization. Mice were anesthetized prior to immunization by intra-peritoneal (IP) route with a mix solution of xylazine 2% (Bayer AG) and ketamine 8% (Imalgen 1000) PBS according to individual animal weight. All animals were housed at Institut Pasteur's animal facility and were handled in agreement with good animal practice and according to the Ethics Charter of Institut Pasteur.

HLA-G $\alpha_3$ Domain Protein and DNA Immunization Protocols

The $\alpha_3$ domain protein (0.1 mg/ml) was dissolved in PBS1x and emulsified in equal volumes of Complete Freund's adjuvant (CFA, Sigma) for the prime immunization and with Incomplete Freund's adjuvant (IFA, Sigma) for subsequent immunization boosts. C57Bl/6J HLA-B*0702 transgenic mice were immunized every two weeks performing intra-dermic (ID) administration of the protein in the dorsal area after shaving, using specific insulin needles U-100. The inventors used non-dimerized forms of SEQ ID No2 for administration. DNA immunization was performed by non-invasive intra-muscular (IM) electroporation. Animals were shaved and aseptically swabbed prior to the immunization. The plasmid was administered in the inferior tibialis cranialis muscle, injecting 50 μl of the plasmid DNA (0.1 mg/ml dissolved in PBS buffer, Invitrogen) in each leg. DNA immunizations were performed as followed; prime DNA immunization was followed 2 weeks after by DNA immunization boosts made every week during 3 weeks. Immunized mice were bleeded at the time of immunization boosts to monitor antibodies presence within plasmas. Immediately following the inoculation, legs were covered with ultrasound gel, and the non-invasive plate electrodes for the Agilepulse™ electroporator (BTX) delivery system applied. A single pulse of 560 V per cm of electrode spacing for 50 ms with a frequency of 1 Hz was applied, and the plate electrodes were 0.5 cm apart.

Sample Analysis

Specific anti-HLA-G $\alpha_3$ domain antibodies were determined on sera or plasma samples. Sera were obtained by orbital sinus bleeding and plasmas were obtained by tail vain bleeding techniques for protein and DNA immunizations respectively. 20-50 μl of blood samples were harvested in heparin microtubes.

Enzyme-Linked Immunosorbent Assay (ELISA)

The presence of anti-HLA-G $\alpha_3$ domain antibodies within the plasmas of protein-immunized mice was analyzed by an indirect colorimetric ELISA. Microtiter plates were coated with synthetic proteins. Sera were serially diluted (from 1/500 to 1/32,000) and added to the plate after blocking and washing. Bound antigen-specific antibodies were detected using 0.1 μg/ml mouse-specific antibodies horse-radish conjugated anti IgG antibodies, incubated in the wells for 1 hour at 37° C. Plates were developed with OPD and read at 405 nm (OD).

Flow Cytometry Analysis (Luminex)

Anti-HLA-G $\alpha_3$ domain antibodies screening in sera and plasma of protein and DNA immunized mice respectively, were performed with Bio-Plex System Bead Coupling (Bio-Rad). One million beads (80 μl) were activated and coupled with 30 μg/ml of HLA-G $\alpha_3$ domain synthetic protein, as previously described [42] and outlined in FIG. 7. Coupled microspheres were counted by a cytometer Epics XL cytometer (Beckman Coulter) to evaluate the final number of beads. For antibody screening, 10 μl of serum sample were added to a 96-well filter microplate (Millipore, Billerica, Mass., USA) and 2 μl of HLA-G $\alpha_3$ domain coated beads were added and incubated in the dark for 30 min at RT. After washing thoroughly with PBS buffer, 50 μl of 20 μg/ml phycoerythrin-conjugated goat anti-mouse IgG Ab (GAM-PE, R&D Systems) secondary antibody was added to the beads and samples were again conjugated for 30 min in the dark at RT. Then, the microspheres were washed by vacuum filtration. All samples were analyzed in duplicate by flow cytometry. The results were presented in median fluorescence intensity (MFI) and the cut-off of positive reactions was defined using sera of non-immunized mice of each cohort.

Slot-Blot Analysis

HLA-G $\alpha_3$ domain protein was blotted onto a nitrocellulose membrane after separation in a 12% SDS-PAGE electrophoresis (GE Healthcare). Membranes were blocked by incubation with PBS containing 0.2% Tween 20 and 5% nonfat dry milk for 1 hour at room temperature (RT). The membranes were then probed with plasmas from protein and plasmid DNA immunized mice, diluted at 1/20 and incubated in a Mini-PROTEAN II Multiscreen apparatus (Bio-Rad) overnight at 4° C. After washing with PBS containing 0.2% Tween 20, membranes were blocked again with PBS containing 0.2% Tween 20 and 5% nonfat dry milk for 20 min. The membranes were subsequently incubated for 1 hour at room temperature with peroxidase-conjugated goat anti-mouse IgG Ab (Sigma), washed thoroughly, stained with enhanced chemiluminescence reagent ECL (GE Healthcare), and exposed to X-ray film.

Results

Anti-HLA-G $\alpha_3$ Domain Protein Antibodies Produced in HLA-B*0702 Transgenic Mice after Protein Immunization.

Figure 7A:
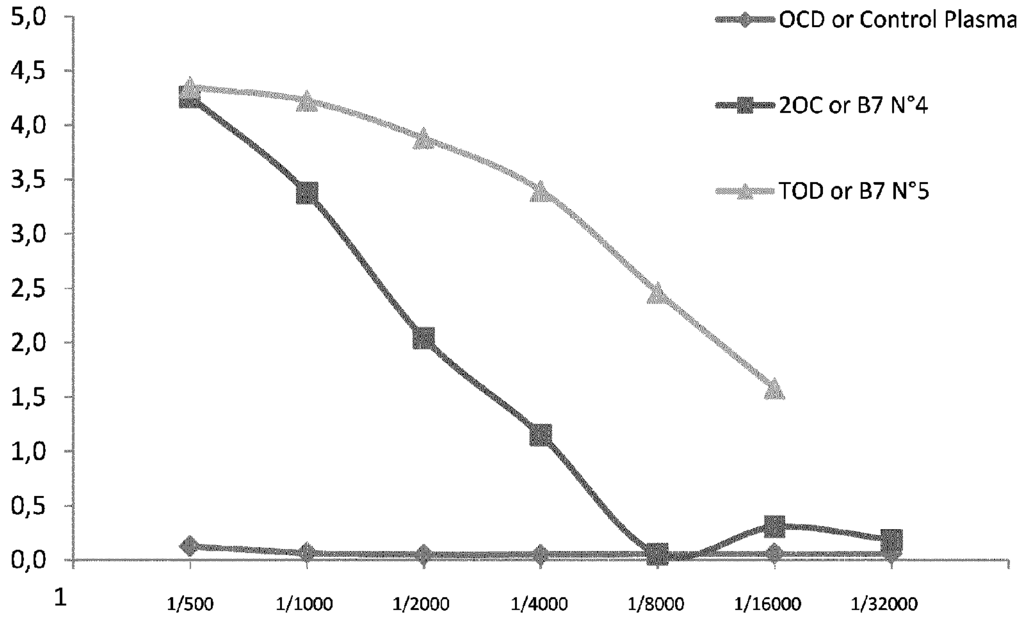
Figure 7B:
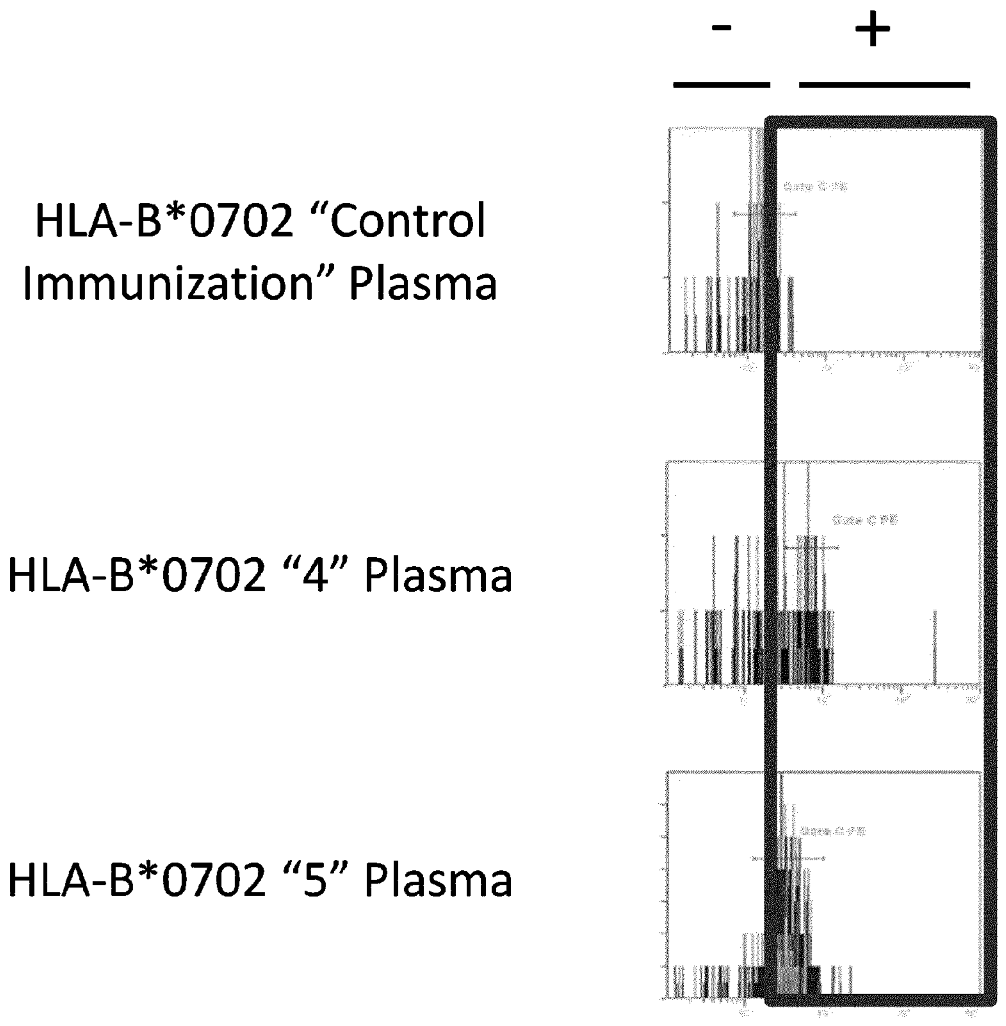
Figure 7C:
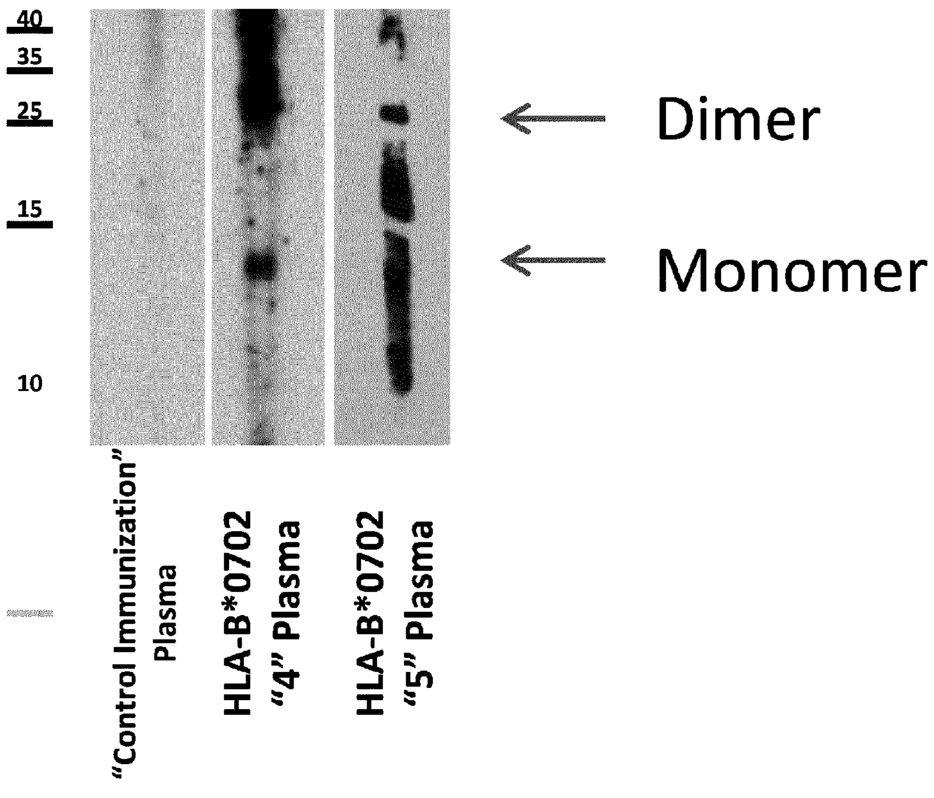

For protein immunization 4 C57Bl/6J HLA-B*0702 transgenic mice were first immunized with the HLA-G $\alpha_3$ domain protein in CFA, and injected every two weeks with the protein in IFA. Sera were tested by ELISA every two weeks after the second immunization. After 8 weeks of immunization, specific antibodies for HLA-G $\alpha_3$ domain protein were detected in one mouse, and another mouse responded after 12 weeks of immunization (the equivalent of 6 boosts), as shown in FIG. 7 (A).

Afterwards, two other methods were performed to monitor antibody secretion, in order to confirm these results. In the first place, a Luminex bead assay (set up and validated for HLA-G by this/SRHI laboratory), was carried out to evaluate the presence of conformational antibodies. As shown in FIG. 7 (B), the plasmas of the C57Bl/6J HLA-B*0702 transgenic mice "4" and "5" were positively bound to the HLA-G $\alpha_3$ domain-coated beads, in accordance with the ELISA results. Interestingly, we observed that the plasma of the C57Bl/6J HLA-B*0702 transgenic mouse "5" by the $8^{th}$ week of immunization was already positive for the Luminex beads assay, and was not positive for ELISA until the $12^{th}$ week. Finally, the presence of HLA-G $\alpha_3$ domain specific antibodies against denatured epitopes was confirmed by a slot-blot assay. Results shown in FIG. 7 (C) indicate a positive result only for plasma of the mouse "4".

Anti-HLA-G $\alpha_3$ Domain Protein Antibodies Produced in Balb/c, C57Bl/6J and HLA-B*0702 Transgenic Mice Following DNA Immunization The second strategy of immunization was set up using DNA coding for the $\alpha_3$ domain of the HLA-G molecules. Three murine strains were immunized with the specific sequence, which was delivered by EGT (Electro-Gene Transfer) in muscular cells. In the case of Balb/c mice, three immunized animals were positive for the Luminex beads assay as well as for the slot-blotting analysis, shown in FIGS. 8 (A) and (B). For the C57Bl/6J strain, three out of four immunized animals were positive as well, for both Luminex beads and Slot-blot assays as shown in FIGS. 9 (A) and (B).

Comparative Experiences with Respect to DNA HLA-G-α3 Vaccination

The inventors also investigated whether DNA-HLA-G a3 domain electroporation could inhibit the immunosuppressive effect of the complete HLA-G molecule. For this purpose, Balb/c mice were electroporated or not with DNA-HLA-G a3 domain and circulating antibodies raised against HLA-G-a3 domain, as described herein, were generated. Non-electroporated and DNA-HLA-G a3 electroporated Balb/c mice were inoculated subcutaneously with $2 \cdot 10^6$ M8 melanoma cells transfected or not with HLA-G1 molecules and respectively referred as M8-HLA-G1 and M8-pcDNA cells [38]. As shown on FIG. 10, without DNA-HLA-G α3-electroporation, M8-HLA-G1 tumor growth was higher than M8-pcDNA cells as previously reported [17]. However, after DNA-HLA-G α3 electroporation, tumor growth was similar between subcutaneously implanted M8-HLA-G1 and M8-pcDNA tumor cells (FIG. 11). Thus, HLA-G1 protective effect was prevented in electroporated mice. The inventors further showed that suppression of HLA-G protective effect on transfected M8-HLA-G1 cells was correlated with the presence of circulating antibodies raised against HLA-G α3 domains in mice sera (data not shown).

Discussion

The inventors have produced anti-HLA-G antibodies by using the HLA-G $\alpha_3$ domain by protein and DNA immunization. DNA immunization proved to be the efficient way to raise antibodies against the $\alpha_3$ domain of HLA-G protein, as illustrated in mice. This strategy was considered relevant to the generation of anti-HLA-G antibodies because the $\alpha_3$ domain of HLA-G contains an unique motif of the molecule, present in no other HLA molecule. According to a particular embodiment, generated anti-HLA-G antibodies of the invention recognize a conformational epitope on HLA-G proteins, as present in HLA-G proteins naturally expressed by the cellular machinery. Furthermore, the use of the HLA-G $\alpha_3$ domain was anticipated to be particularly relevant to the generation of blocking antibodies, because the function of HLA-G is dependent on the association between LILRB molecules and the $\alpha_3$ domain of HLA-G, even though additional binding to β2M is required for the LILRB1 receptor. However, as discussed above, all attempts to target said HLA-G $\alpha_3$ domain by producing anti-HLA $\alpha_3$ domain antibodies have failed so far. Finally, this strategy represents a significant advance because the antibody produced will be able to recognize β2M-associated, β2M-free, and truncated HLA-G isoforms, which all contain the $\alpha_3$ domain and are all immune-inhibitory and pathologically relevant.

Two methods were implemented, which allowed efficient immunization of most HLA-G isoforms using a DNA sequence and an engineered protein corresponding to the HLA-G $\alpha_3$ domain. These innovative immunization strategies allowed the development and production of anti-HLA-G antibodies, which are fundamental to anti-HLA-G-tumor based therapies and HLA-G monitoring.

The inventors have demonstrated by three different detection methods, that it was possible to produce new anti HLA-G antibodies by immunization of HLA-B*0702 transgenic mice with the $\alpha_3$ domain of HLA-G. The difference observed amongst the ELISA, Luminex beads and the slot-blot assays can be explained by the fact that the last method utilizes denatured epitopes, for which some of the clones producing antibodies, detected in the other assays, do not recognize such epitope. Hence, some polyclonal antibodies could bind to denatured epitopes while others could bind to conformational ones.

A different strategy was also performed with the purpose of producing specific anti-HLA-G α3 domain antibodies through DNA immunization. DNA immunization yielded 3/6 for the strain Balb/c and 3/4 positive results for the C57Bl/6J strain, detected by both Luminex and slot-blot assays.

In DNA HLA-G-α3 vaccination experiments, the inventors have proved that Balb/c mice generated anti-HLA-G-α3 antibodies after DNA immunization, with a strong effect on the tumor growth.

REFERENCES

1. Geraghty, D. E., B. H. Koller, and H. T. Orr, *A human major histocompatibility complex class I gene that encodes a protein with shortened cytoplasmic segment*. Proc. Natl. Acad. Sci. USA, 1987. 84(1): p. 9145-9149.
2. Ellis, S. A., M. S. Palmer, and A. J. McMichael, *Human trophoblast and the choriocarcinoma cell line BeWo express a truncated HLA Class I molecule*. J Immunol, 1990. 144(2): p. 731-5.
3. Rouas-Freiss, N., et al., *The alpha1 domain of HLA-G1 and HLA-G2 inhibits cytotoxicity induced by natural killer cells: is HLA-G the public ligand for natural killer cell inhibitory receptors*? Proc Natl Acad Sci USA, 1997. 94(10): p. 5249-54.
4. Carosella, E. D., et al., *Beyond the increasing complexity of the immunomodulatory HLA-G molecule*. Blood, 2008. 111(10): p. 4862-70.
5. Rouas-Freiss, N., et al., *Direct evidence to support the role of HLA-G in protecting the fetus from maternal uterine natural killer cytolysis*. Proc Natl Acad Sci USA, 1997. 94(21): p. 11520-5.
6. Riteau, B., et al., *HLA-G2, -G3, and -G4 isoforms expressed as nonmature cell surface glycoproteins inhibit NK and antigen-specific CTL cytolysis*. J Immunol, 2001. 166(8): p. 5018-26.
7. Riteau, B., et al., *HLA-G inhibits the allogeneic proliferative response*. J Reprod Immunol, 1999. 43(2): p. 203-11.
8. Bainbridge, D. R., S. A. Ellis, and I. L. Sargent, *HLA-G suppresses proliferation of CD4(+) T-lymphocytes*. J Reprod Immunol, 2000. 48(1): p. 17-26.
9. Bahri, R., et al., *Soluble HLA-G inhibits cell cycle progression in human alloreactive T lymphocytes*. J Immunol, 2006. 176(3): p. 1331-9.
10. LeMaoult, J., et al., *Immune regulation by pretenders: cell-to-cell transfers of HLA-G make effector T cells act as regulatory cells*. Blood, 2007. 109(5): p. 2040-8.
11. Caumartin, J., et al., *Trogocytosis-based generation of suppressive NK cells*. EMBO J, 2007. 26(5): p. 1423-33.
12. Ristich, V., et al., *Tolerization of dendritic cells by HLA-G*. Eur J Immunol, 2005. 35(4): p. 1133-42.
13. Gros, F., et al., *Soluble HLA-G molecules impair natural killer/dendritic cell crosstalk via inhibition of dendritic cells*. Eur J Immunol, 2008. 38(3): p. 742-9.
14. Liang, S., et al., *Modulation of dendritic cell differentiation by HLA-G and ILT4 requires the IL-6-STAT3 signaling pathway*. Proc Natl Acad Sci USA, 2008. 105 (24): p. 8357-62.
15. LeMaoult, J., et al., *HLA-G1-expressing antigen-presenting cells induce immunosuppressive CD4+ T cells*. Proc Natl Acad Sci USA, 2004. 101(18): p. 7064-9.
16. Gregori, S., et al., *Differentiation of type 1 T regulatory cells (Tr1) by tolerogenic DC-10 requires the IL-10-dependent ILT4/HLA-G pathway*. Blood, 2010. 116(6): p. 935-44.
17. Agaugue, S., E. D. Carosella, and N. Rouas-Freiss, *Role of HLA-G in tumor escape through expansion of myeloid-derived suppressor cells and cytokinic balance in favor of Th2 versus Th1/Th17*. Blood, 2011. 117(26): p. 7021-31.
18. Carosella, E. D., et al., *HLA-G: from biology to clinical benefits*. Trends Immunol, 2008. 29(3): p. 125-32.
19. Ibrahim, E. C., et al., *Analysis of HLA antigen expression in benign and malignant melanocytic lesions reveals that upregulation of HLA-G expression correlates with malignant transformation, high inflammatory infiltration and HLA-A1 genotype*. Int J Cancer, 2004. 108(2): p. 243-50.
20. Riteau, B., et al., *HLA-G2, -G3, and -G4 isoforms expressed as nonmature cell surface glycoproteins inhibit NK and antigen-specific CTL cytolysis*. J Immunol, 2001. 166(8): p. 5018-26.
21. Paul, P., et al., *HLA-G expression in melanoma: a way for tumor cells to escape from immunosurveillance*. Proc Natl Acad Sci USA, 1998. 95(8): p. 4510-5.
22. Nuckel, H., et al., *HLA-G expression is associated with an unfavorable outcome and immunodeficiency in chronic lymphocytic leukemia*. Blood, 2005. 105(4): p. 1694-1698.
23. Qiu, J., et al., *Soluble HLA-G expression and renal graft acceptance*. Am J Transplant, 2006. 6(9): p. 2152-6.
24. Naji, A., et al., *Neoplastic B-cell growth is impaired by HLA-G/ILT2 interaction*. Leukemia, 2012.
25. Hunt, J. S., et al., *Immunogenicity of the soluble isoforms of HLA-G*. Mol Hum Reprod, 2003. 9(11): p. 729-35.
26. Le Rond, S., et al., *Alloreactive CD4+ and CD8+ T cells express the immunotolerant HLA-G molecule in mixed lymphocyte reactions: in vivo implications in transplanted patients*. Eur J Immunol, 2004. 34(3): p. 649-60.

27. Lila, N., et al., *Soluble HLA-G protein secreted by allo-specific CD4+ T cells suppresses the allo-proliferative response: a CD4+ T cell regulatory mechanism*. Proc Natl Acad Sci USA, 2001. 98(21): p. 12150-5.
28. Favier, B., et al., *Tolerogenic function of dimeric forms of HLA-G recombinant proteins: a comparative study in vivo*. PLoS One, 2011. 6(7): p. e21011.
29. HoWangYin, K. Y., et al., *Multimeric structures of HLA-G isoforms function through differential binding to LILRB receptors*. Cell Mol Life Sci, 2012.
30. Cooper, M. A., T. A. Fehniger, and M. A. Caligiuri, *The biology of human natural killer-cell subsets*. Trends Immunol, 2001. 22(11): p. 633-40.
31. Rajagopalan, S. and E. O. Long, *A human histocompatibility leukocyte antigen (HLA)-G-specific receptor expressed on all natural killer cells*. J Exp Med, 1999. 189(7): p. 1093-100.
32. Yan, W. H. and L. A. Fan, *Residues met76 and gln79 in HLA-G alpha1 domain involve in KIR2DL4 recognition*. Cell Res, 2005. 15(3): p. 176-82.
33. Colonna, M., et al., *A common inhibitory receptor for major histocompatibility complex class I molecules on human lymphoid and myelomonocytic cells*. J. Exp. Med., 1997. 186(11): p. 1809-1818.
34. Colonna, M., et al., *Human myelomonocytic cells express an inhibitory receptor for classical and nonclassical MHC class I molecules*. J. Immunol., 1998. 160(7): p. 3096-3100.
35. Allan, D. S., et al., *Tetrameric complexes of human histocompatibility leukocyte antigen (HLA)-G bind to peripheral blood myelomonocytic cells*. J Exp Med, 1999. 189(7): p. 1149-56.
36. Colonna, M., et al., *Human myelomonocytic cells express an inhibitory receptor for classical and nonclassical MHC class I molecules*. J Immunol, 1998. 160(7): p. 3096-100.
37. Shiroishi, M., et al., *Efficient leukocyte Ig-like receptor signaling and crystal structure of disulfide-linked HLA-G dimer*. J Biol Chem, 2006. 281(15): p. 10439-47.
38. Caumartin, J., et al., *Trogocytosis-based generation of suppressive NK cells*. EMBO J, 2007. 26: p. 1423-1433.
39. Shiroishi, M., et al., *Structural basis for recognition of the nonclassical MHC molecule HLA-G by the leukocyte Ig-like receptor B2 (LILR82/LIR2/ILT4/CD85d)*. Proc Natl Acad Sci USA, 2006. 103(44): p. 16412-7.
40. Gonen-Gross, T., et al., *The CD85J/Leukocyte Inhibitory Receptor-1 Distinguishes between Conformed and {beta}2-Microglobulin-Free HLA-G Molecules*. J. Immunol., 2005. 175(8): p. 4866-4874.
41. Shiroishi, M., et al., *Structural basis for recognition of the nonclassical MHC molecule HLA-G by the leukocyte Ig-like receptor B2 (LILR82/LIR2/ILT4/CD85d)*. PNAS, 2006. 103(44): p. 16412-16417.
42. Rebmann, V., et al., *Rapid evaluation of soluble HLA-G levels in supernatants of in vitro fertilized embryos*. Hum Immunol, 2007. 68(4): p. 251-8.

The invention claimed is:

1. A method of producing an antibody or an antigen-binding fragment thereof which specifically binds the α3 domain of a HLA-G protein, the method comprising administering to a mammal a nucleic acid molecule encoding a polypeptide comprising the amino-acid sequence of SEQ ID NO: 1, or an amino-acid sequence comprising at least 99% amino acid identity over the entirety of SEQ ID NO: 1.

2. The method of claim 1, wherein the antibody or antigen-binding fragment thereof which specifically binds the α3 domain of a HLA-G protein is a blocking antibody or antigen-binding fragment thereof.

3. The method according to claim 1, further comprising recovering antibodies elicited by said mammal from sera or plasma obtained from said mammal.

4. The method of claim 3, further comprising preparing antigen-binding fragments from the recovered antibodies.

5. The method according to claim 3, further comprising checking the recovered antibodies for specificity to the α3 domain of the HLA-G protein.

6. The method according to claim 3, further comprising preparing antigen-binding fragments from the recovered antibodies.

7. The method according to claim 1, wherein the mammal is a non-human mammal.

8. The method according to claim 1, wherein said antibody or antigen-binding fragment binds the α3 domain of a HLA-G protein when the α3 domain is in a monomeric and/or a dimeric form.

9. The method according to claim 1, wherein said antibody or antigen-binding fragment binds the α3 domain when present in the HLA-G protein.

10. The method according to claim 1, wherein said antibody or antigen-binding fragment binds the α3 domain when present in a β2-microglobulin free HLA-G protein or HLA-G protein isoform.

11. The method according to claim 1, wherein said antibody or antigen-binding fragment does not bind the α3 domain when the HLA-G protein is associated with the β2-microglobulin.

12. The method according to claim 1, wherein said antibody or antigen-binding fragment blocks binding of a HLA-G protein to at least one of LILRB1 and LILRB2 receptors.

13. The method according to claim 1, wherein said nucleic acid molecule comprises the nucleic acid sequence of SEQ ID NO: 9, SEQ ID NO: 10, or SEQ ID NO: 6.

14. The method according to claim 1, wherein said nucleic acid molecule is administered to the mammal in the form of naked DNA.

15. The method according to claim 1, wherein said nucleic acid molecule is administered to the mammal by a delivery method selected from the group consisting of intramuscular or intradermal injection, electroporation, gene-gun delivery, needle-free delivery system, topical administration, and a combination thereof.

16. The method according to claim 1, further comprising administering an adjuvant to the mammal.

17. The method according to claim 1, wherein the nucleic acid molecule encodes a polypeptide comprising the amino-acid sequence of SEQ ID NO: 2.

18. The method according to claim 1, wherein the nucleic acid molecule encodes a polypeptide comprising the amino-acid sequence of SEQ ID NO: 1.

* * * * *